US006878745B2

(12) United States Patent
Ishibashi et al.

(10) Patent No.: US 6,878,745 B2
(45) Date of Patent: Apr. 12, 2005

(54) SELECTIVE PREVENTIVES/REMEDIES FOR PROGRESSIVE LESIONS AFTER ORGAN DAMAGE

(75) Inventors: Michio Ishibashi, 25-16, Niwashirodai 4-cho, Sakai-shi, Osaka 590-0133 (JP); Alain Wagner, Strasbourg (FR); Charles Mioskowski, Strasbourg (FR); Catherine Sylvain, Gevrey-Chambertin (FR)

(73) Assignee: Michio Ishibashi, Osaka (JP)

( * ) Notice: Subject to any disclaimer, the term of this patent is extended or adjusted under 35 U.S.C. 154(b) by 0 days.

(21) Appl. No.: 10/239,783

(22) PCT Filed: Mar. 27, 2001

(86) PCT No.: PCT/JP01/02513

§ 371 (c)(1),
(2), (4) Date: Dec. 12, 2002

(87) PCT Pub. No.: WO01/72730

PCT Pub. Date: Oct. 4, 2001

(65) Prior Publication Data

US 2003/0181506 A1 Sep. 25, 2003

(30) Foreign Application Priority Data

Mar. 28, 2000 (JP) ......................................... 2000-88990
Sep. 22, 2000 (JP) ....................................... 2000-289458

(51) Int. Cl.$^7$ ..................... A61K 31/34; A61K 31/585
(52) U.S. Cl. ..................... 514/461; 514/175; 514/470
(58) Field of Search ................................. 514/175, 461, 514/470

(56) References Cited

FOREIGN PATENT DOCUMENTS

| JP | 45-20956 | 7/1970 |
| JP | 04-338331 | 11/1992 |

OTHER PUBLICATIONS

J.L. Derrick Clive et al., "Synthesis of the Angiotensin–Converting Enzyme Inhibitors (–)–A58365A and (–)–A583658 from a Common Intermediate", J. Org. Chem., vol. 64, No. 5, pp. 1447–1454, 1999, chemical compound 9.
M. Ishibashi et al., Cellular Immune Response Against Human Red Blood Cell Antigens and Renal Allograft Rejection. Transplant Proc, 1987, 19:4511–4515.
M. Ishibashi et al., Immunologic Studies of Red Cell Antigens in the Renal Transplant Patient. Transplant Proc, 1984, 16:1509–1511.
M. Ishibashi et al., Monocyte–mediated Hemolytic Response in Renal Transplant Patients. Transplant Proc, 1985, 17: 2644–2647.
M. Ishibashi et al., Novel Effector Moncytes Against Human RBC Antigens Invading Rejected Renal Allografts. Transplant Proc, 1988, 20: 285–288.
M. Ishibashi et al., Immunologic Effects of Immunosuppressive Agents Explored by a New Effector Monocyte Generation Assay. Transplant Proc, 1989, 21: 1854–1858.
M. Ishibashi et al., A Gamma–lactone Immunosuppressant Inhibits the Generation of Macrophage Killer Cells and Prolonged skin Allograft Survival in the Rat. Transplant Proc, 1992, 24: 1411–1412.
A. Moutabarrik et al., Monocyte Hemolytic Activity as an Immunologic Indicator of Allograft Rejection in Rat Skin Transplantation. Transplant Proc, 1992, 24: 403–407.
M. Ishibashi et al., Nonspecific Hemolytic Effector of Activated Macrophages as Activation Marker of Allograft Rejection. Transplant Int, 1992, 5 (Suppl. 1): S290–S295.
M. Ishibashi et al., Prevention of Chronic Rejection of Renal Allografts in Rat Using a Synthetic Inhibitor of Macrophage Effector Activation. Transplant Proc, 1995, 27: 564–565.
H. Azuma et al., Prevention of Functional, Structural and Molecular Changes of Chronic Rejection of Rat Renal Allografts by a Specific Macrophage Inhibitor. Transplantation, 1995, 60: 1577–1582.
M. Ishibashi et al., Prevention of Chronic rejection and Puromycin–induced Giomerulosclerosis in Rats by Gamma–Lactone, as an Inhibitor of Macrophage–effector Activation. Transplant Proc, 1996, 28: 953–954.
M. Ishibashi et al., Attenuation of Glomerular Epithelial Cell Innury and Diminution of Tubulointerstitial Lesions by a Macrophage Inhibitor in Chronic Puromycin–nephrosis model. Nephrology, 1997; 3 (Suppl. 1): S44.
M. Ishibashi et al., Combined use of Selective Inhibitor of Macrophage–effector Generation for Treatment of Differential Glomerular and Tubulointerstitial Lesion of Progressive Renal Diseases. Abstract submitted to the 35th Amer. Soc. of Nephrology, Pennsylvania, Oct. 30–Nov. 4, 2002.

*Primary Examiner*—Kevin E. Weddington
(74) *Attorney, Agent, or Firm*—Wenderoth, Lind & Ponack, L.L.C.

(57) ABSTRACT

Drugs for preventing and/or treating progressive lesions after organ damage without inhibiting the function of the organ or the regeneration function thereof, by selectively regulating the induction of cytotoxic effecter macrophages which are induced into damaged organ tissues in response to chemokines or cytokines expressed depending on the type of the damaged organ tissues.

6 Claims, No Drawings

SELECTIVE PREVENTIVES/REMEDIES FOR PROGRESSIVE LESIONS AFTER ORGAN DAMAGE

This application is a 371 of PCT/JP01/02513 filed Mar. 27, 2001.

TECHNICAL FIELD

Organs in organism may be damaged, for example, by blood flow disorder, ischemia reperfusion injury, hypertension, hyperglycemia, hyperlipemia, pharmaceutical agent or viral infection. Damaged organ tissues show any of responses of necrosis, natural death or self-regeneration depending upon the degree of the damage. Immune system deeply participates in such a response and some of macrophages which are carriers of such immune participate in self-regeneration of organ tissues while others participate in necrosis or natural death of organ tissues. The latter, i.e. that which shows cytotoxicity in a functional manner among the much differentiated macrophages, is called effector macrophage and such an effector macrophage further worsens the damage after the above-mentioned damage and causes a progressive lesion after the organic damage.

The present invention relates to a pharmaceutical in which induction of effector macrophage which is a cause of progressive lesion noted after such an organic damage is selectively suppressed whereby the said progressive lesion is prevented and/or treated without inhibiting the function and regeneration process of the organ, and also relates to a therapeutic method using the same. The present invention further relates to a screening method for compounds which can be the said pharmaceutical. The present invention still further relates to novel γ-lactone derivatives useful as the said pharmaceutical.

With regard to one of the progressive lesions noted after the above-mentioned organic damages, fibrosis of tissue cells may be exemplified. Such a fibrosis of tissue cells is caused by effector macrophage showing cytotoxic property the same as above. The novel γ-lactone derivatives according to the present invention are able to selectively suppress the induction of the said effector macrophage. As a result of utilization of such an action, the present invention also relates to a pharmaceutical as a fibrosis inhibitor containing the said novel γ-lactone derivative.

Rejection, particularly chronic rejection, upon transplantation of allogenic or xenogenic organ cells is caused by the same mechanism in the progressive lesion after organic damage or, at least similar, mechanism to that. The novel γ-lactone derivatives according to the present invention selectively suppress the induction of effector macrophage causing the induction of allograft rejection, particularly chronic rejection, upon allogenic or xenogenic cell, tissue or organ transplantation whereby they show an immunosuppressive action only in the organ tissues showing the rejection. As a result of utilization of such an action, the present invention also relates to a pharmaceutical as an immunosuppressant containing the said novel γ-lactone derivative.

BACKGROUND OF THE INVENTION

When an organ in organisms is damaged, for example, by blood flow disorder, ischemia reperfusion injury, hypertension, hyperglycemia, hyperlipemia, pharmaceutical agent or viral infection, there works an organism defense mechanism by, for example, T lymphocytes, macrophages, NK cells, fibroblasts, B lymphocytes and antibodies, complements, etc. Particularly, T cells and macrophages have an important participation in the said organism defense mechanism.

Damaged organ tissues show any of the responses of necrosis, natural death or self-regeneration depending upon the degree of the damage. At that time, chemokines, cytokines, etc. are expressed from the said tissues to promote self-proliferation and regeneration and, at the same time, organism defense mechanism of the host is activated as well. It has been presumed that the outcome whether the damaged tissues result in necrosis or natural death by way of atrophy and fibrosis or they result in regeneration of tissues is the result of the interaction of both.

For example, there are several reports for the studies that, in the damaged renal tissue lesions, the damaged renal tissue cells express tissue-specific chemokine, cytokine or adhesion factor depending upon the damaged area, etc. whereby the response is exhibited.

Wada, et al. reported that, in human crescentic glomerulonephritis, MIP-1α of chemokine is expressed in glomerular cellular crescents in an acute stage while, in interstitial tissues of the cases of fibrous crescents in a chronic stage, MCP-1 is expressed (Wada T., Furuichi K., Segawa-Takeda C., Shimizu M., Sakai N., Takeda S. I., Takasawa K., Kida H., Kobayashi K. I., Mukaida N., Ohmoto Y., Matsushima K., Yokoyama H.: MIP-1α and MCP-1 contribute to crescents and interstitial lesions in human crescentic glomerulonephritis. *Kidney Int.*, 56: 995–1003, 1999.

Matsuda, et al. reported that, in model rats suffering from crescentic glomerulonephritis, P-secretin and L-secretin are expressed in a discriminated manner in glomerular endothelial cells and in interstitial tissues from urinary tubule, respectively (Michihiro Matsuda, Kenichi Shikata, Daisuke Ogawa, Shinichi Okada, Yasushi Shikata, Atsushi Wada. and Hiroshi Makino: Mechanism of Induction of Infiltration of Leucocytes to Renal Tissues by Secretin, *Nippon Jinzo Gakkaishi*, 42: 213, 2000).

Tesch, et al. reported that, when nephrotoxic serum nephritis model was prepared in MCP-1 knockout mice and expression of MCP-1 was checked, the expression of MCP-1 in the damaged site of urinary tubule was weak as compared with a wild type while the expression of MCP-1 in the glomerular lesion had no difference from the wild type. They also reported that, in the knockout mice where expression of MCP-1 was weak, infiltration of macrophage decreased whereby MCP-1 showed the result that it participated in migration of macrophage while, in terms of degree of proteinuria in an acute stage, there is no difference between both and there was no relation between tissue damage and macrophage infiltration in an acute stage (Tesch G. H., Schwarting A., Kinoshita K., Rolins B. J., Kelly V. R.: Monocyte chemoattractant protein-1 promotes macrophage-mediated tubular injury, but not glomerular injury, in nephritic serum nephritis, *J. Clin. Invest.* 1999, 103: 73–80.).

Not only in kidney but also in exocrine gland and islet of Langerhans of pancreas, there is noted a difference in chemokine-productive response concerning the lesion after the organ tissue damage corresponding to the damaged tissue.

Cameron, et al. reported that, in the mice where nonobese type I diabetes was spontaneously occurred, promotion of the expression of MIP-1α and lowering of the expression of MCP-1 were noted among chemokines in islets of Langerhans and that there was a correlation between damage of islets of Langerhans and onset of diabetes (Cameron M. J., Arreaza G. A., Grattan M., Meagher C., Sharif S., Burdick M. D., Strieter R. M., Cook D. N., Delovitch T. L.: Differential expression of CC chemokines and the CCR5 receptor in the pancreas is associated with progression to type I diabetes, *J. Immunol.*, 2000, 165: 1102–10).

In the meanwhile, Andoh, et al. investigated the expression of chemokines in pancreatitis tissues of human acute pancreatitis cases. They reported that, in acute pancreatitis, expression of MIP-1α was not noted but expression of MCP-1, IL-8 and RANTES was noted in exocrine, acinar and ductal interstitial pancreas tissues (Andoh A., Takaya H., Saotome T., Shimada M., Hata K., Araki Y., Nakamura F., Shintani Y., Fujiyama Y., Bamba T.: Cytokine regulation of chemokine (IL-8, MCP-1, and RANTES) gene expression in human pancreatic periacinar myofibroblasts, *Gastroenterology*, 2000, 119: 211–9).

As mentioned above, it was suggested in human clinical studies and experimental study models using animals that, in progressive lesion noted after the organic damage, effector macrophage participated therein corresponding to the damaged tissues.

Up to now, therapy of steroids, etc. has been carried out for progressive lesion after organic damage. However, since steroidal preparations non-selectively suppress the macrophage, they also suppress the response of even the macrophage participating in the reaction for tissue regeneration at the same time whereby organism defensive mechanism including the regeneration is lessened. In addition, new tissue damage is induced resulting in lesion and, as a result, there is a problem that effector macrophage mediated by the expression of chemokines and cytokines is actively induced whereby the inherent lesion is further worsened. As such, the conventional therapy of steroids has no selectivity in the action, and administration of high dose is necessary for the therapy of the lesion whereby the side effect is remarkable. In addition, there is a difficulty that a continuous therapy by steroids for a long period is accompanied by a severe side effect.

On the other hand, like the progressive lesion noted after the above-mentioned organic damage, organism defense mechanism by T cells, macrophages, etc. participates in rejection in the transplantation of organ, skin or the like. Until now, there have been known many compounds having an immunosuppressive action and, for example, compounds represented by the formula (8)

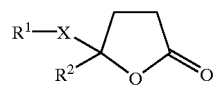

(8)

(in which $R^1$ is an optionally substituted phenyl group; $R^2$ is an optionally esterified carboxyl group; and X is oxygen atom or optionally oxidized sulfur atom) have been known to be useful as a γ-lactone immunosuppressant (Japanese Patent Laid-Open No. 04/338,331). However, it is to be still improved so as to show a selective action to target organs or tissues or so as to show stronger immunosuppressive action.

DISCLOSURE OF THE INVENTION

Effector macrophage expresses chemokine receptors or β2 integrin receptors, etc. corresponding to the lesion inherent to the tissues after the organic damage via either T-lymphocyte-independent or T-lymphocyte-dependent response and is selectively induced to and activated in lesion being mediated by them whereby said effector macrophage causes a progressive lesion after the tissue damage. An object of the present invention is to provide a pharmaceutical in which expression and function of chemokine receptors such as CCR2, CCR3 or CCR8, β2 integrin receptors such as CD11b/CD18 or other receptors are suppressed to selectively suppress the induction of the above-mentioned effector macrophages whereby progressive lesion after organic damage is prevented and/or treated without inhibiting the function of the organ and the regeneration function and also to provide a therapeutic method using the same. Since the pharmaceutical according to the present invention is able to suppress the induction of effector macrophages causing the progressive lesion after organic damage in a more lesion-selectively manner, it is possible to use in a high dose and, due to the selectivity of the said pharmaceutical, undesirable side effect can be avoided even when it is used in a high dose. Therapy for a long period using the said pharmaceutical is now possible as well. Further, when the lesions are different resulting in progressive lesion after the organic damage in plural tissues, it is possible to carry out more selective and more effective therapy by combination use of the above pharmaceuticals showing different selectivity. That is an advantage which is not noted in the conventional steroidal agents and known γ-lactone immunosuppressants having no selectivity. The present invention also aims to provide useful and novel γ-lactone derivatives.

Another object of the present invention is to provide a method for screening the compounds which do not substantially suppress the macrophage participating in tissue regeneration and cause the progressive lesion after the above-mentioned organic damage.

Still another object of the present invention is to provide a method for inducing the effector macrophage which causes the progressive lesion after the above-mentioned organic damage.

Further object of the present invention is to provide a pharmaceutical useful as a fibrosis inhibitor preventing from the fibrosis which is one of lesions inherent to the tissues after the organic damage or, to be more specific, to provide a fibrosis inhibitor containing the above-mentioned novel γ-lactone derivative.

Still further object of the present invention is to provide a pharmaceutical which are useful as an immunosuppressant or, to be more specific, to provide an immunosuppressant which is an immunosuppressant containing the above-mentioned novel γ-lactone derivative and shows a selective immunosuppressive action to target organs or tissues unlike the known γ-lactone immunosuppressants.

As mentioned above, damaged tissue cells express chemokine, cytokine or adhesion molecule inherent to the tissue. Depending upon type or degree (amount) of the expression or upon defense mechanism of organism, the expressed chemokine, cytokine, etc. either promote self-proliferation or regeneration of the damaged tissues or subject the damaged tissue to necrosis, natural death or degeneration. Here, effector macrophage showing cytotoxic property is selectively induced corresponding to type or expressed amount of the said chemokine and cytokine so that the damaged tissues are subjected to necrosis, natural death or degeneration. To be more specific, effector macrophage is selectively induced to the damaged organ tissues (lesion tissues) by chemokine receptors corresponding to the said chemokine expressed in the damaged organ tissues (lesion tissue) or by β2 integrin, etc. corresponding to a ligand expressed on the said organ tissues (lesion tissues). The induced effector macrophage recognizes the damaged tissues, acts on the said tissues in a cytotoxic manner and induces the progressive lesion after the organic damage. On the other hand, the effector macrophage does not recognize the normal tissue wherein chemokine and cytokine which stimulate for inducing and activating the said effector macrophage are not expressed and, as a result, the normal tissue is not damaged.

Accordingly, if induction of effector macrophage in the damaged organ tissues can be selectively suppressed by way of suppression of expression and function of chemokine receptor such as CCR2, CCR3 and CCR8, β2 integrin receptors such as CD11b/CD18 and other receptors, action of the effector macrophage in a cytotoxic manner to the damaged organ tissues can be prevented and, in addition, induction of the macrophage participating in the tissue regeneration is not suppressed so that lowering of the defense ability of the organism is not noted whereby it has been found that progressive lesion after organic damage can be prevented, mitigated or treated.

When a compound which is able to selectively suppress the induction of effector macrophage as such is used as a pharmaceutical, there is reduced the side effect such as that defense of organism is unnecessarily lowered or new tissue damage is induced. In addition, it is possible to result in recovery and regeneration of the tissue without an unnecessary lowering of defense of organism and, therefore, it is now possible to continuously carry out the therapy for a long period.

Ishibashi who is one of the inventors of the present invention has carried out a further investigation for the progressive lesion in kidney on the basis of the above finding and has obtained an unexpected finding that a compound which suppresses the induction of effector macrophage caused by contact of human peripheral blood mononuclear cells abbreviated as PBMC with lipopolysaccharide suppresses the progress of glomerular lesion of kidney and that a compound which suppresses the induction of effector macrophage caused by contact of human PBMC with mitomycin-treated human PBMC suppresses the progress of progressive lesion of tubulointerstitial tissue after renal damage.

Ishibashi who is one of the inventors of the present invention has also carried out an investigation for progressive lesion in pancreas and obtained an unexpected finding that a compound which suppresses the induction of effector macrophage caused by contact of human PBMC with lipopolysaccharide suppresses the progress of lesion in islets of Langerhans of pancreas and that a compound which suppresses the induction of effector macrophage caused by contact of human PBMC with mitomycin-treated human PBMC suppresses the progress of lesion of exocrine, acinar and ductal interstitial tissues of pancreas.

Here, when lesion of islets of Langerhans of pancreas progresses, diabetes mellitus is able to occur. When diabetes mellitus occurs, diabetic nephropathy which is a glomerular lesion is able to occur as a complication thereof. Ishibashi who is one of the inventors of the present invention has further obtained an unexpected finding that a compound which suppresses the induction of effector macrophage caused by contact of human PBMC with lipopolysaccharide is also able to prevent and/or treat the onset of diabetic glomerular lesion (another name: diabetic nephropathy) together with the onset of diabetes mellitus.

Ishibashi who is one of the inventors of the present invention has furthermore obtained an unexpected finding that a compound which suppresses the induction of effector macrophage caused by contact of human PBMC with mitomycin-treated human PBMC is also able to prevent and/or treat the onset of lesion of tubulointerstitial tissues which is a complication of pancreatitis together with onset of pancreatitis which is lesion of exocrine, acinar and ductal interstitial tissues of pancreas.

The present inventors have carried out an investigation for the compounds which are able to selectively suppress the induction of effector macrophage which is caused corresponding to lesion inherent to tissues after the organic damage and, as a result, they have found that novel γ-lactone derivatives represented by the following formulae of from (1) to (7) have such an action.

The present inventors have further found that, since fibrosis of tissues is one of the progressive lesions after the organic damage, the novel γ-lactone derivatives represented by the following formulae of from (1) to (7) are also useful as inhibitors for fibrosis.

With regard to the rejection at the transplantation of organ cells of allogeneic or xenogenic type, there are acute rejection and chronic rejection and it has been known that, particularly in the chronic rejection, not only immunological factors but also non-immunological factors such as damage by pharmaceuticals, ischemia reperfusion injury, viral infection, blood flow disorder and exclusion of cells can be a cause. On the other hand, the above-mentioned progressive lesion after organic damage also results from the organic damage, which is a trigger, such as damage by pharmaceuticals, ischemia reperfusion injury, viral infection, blood flow disorder and exclusion of cells. Accordingly, chronic rejection is caused by a mechanism which is the same as or at least similar to the progressive lesion after the organic damage. Therefore, it has been found that novel γ-lactone derivatives represented by the following formulae of from (1) to (7) which are able to selectively suppress the induction of effector macrophage induced being correspondent to the lesion inherent to the tissues after organic damage are useful as an immunosuppressant for the prevention or the therapy of rejection upon of allogeneic or xenogenic cell, tissue or organ transplantation, particularly as an immunosuppressant to chronic rejection.

Thus, the present invention relates to the followings.

(1) A pharmaceutical composition, which comprises a compound suppressing the induction of effector macrophages.

(2) A preventive and therapeutic pharmaceutical selectively to progressive lesion of organic damages which comprises a compound suppressing the induction of effector macrophages.

(3) A pharmaceutical for prevention and/or therapy of glomerular lesion of kidney, which comprises a compound suppressing the induction of effector macrophages caused by contact of human PBMC with lipopolysaccharide.

(4) A pharmaceutical for prevention and/or therapy of progressive tubulointerstitial lesion after renal damage, which comprises a compound suppressing the induction of effector macrophages caused by contact of human PBMC with mitomycin-treated human PBMC.

(5) A pharmaceutical for prevention and/or therapy of lesion of islets of Langerhans of pancreas, which comprises a compound suppressing the induction of effector macrophages caused by contact of human PBMC with lipopolysaccharide.

(6) A pharmaceutical for prevention and/or therapy of lesion of exocrine, acinar and ductal interstitial tissues of pancreas, which comprises a compound suppressing the induction of effector macrophages caused by contact of human PBMC with mitomycin-treated human PBMC.

(7) A pharmaceutical for prevention and/or therapy of diabetes mellitus and diabetic glomerular lesion, which comprises a compound suppressing the induction of effector macrophages caused by contact of human PBMC with lipopolysaccharide.

(8) A pharmaceutical for prevention and/or therapy of pancreatitis and lesion of interstitial tissues of urinary tubule which is a complication of pancreatitis, which comprises a compound suppressing the induction of effector macrophages caused by contact of human PBMC with mitomycin-treated human PBMC.

(9) A method for prevention and/or therapy of glomerular lesion of kidney, lesion of islets of Langerhans of pancreas or diabetes mellitus and diabetic glomerular lesion, which comprises using a pharmaceutical containing a compound suppressing the induction of effector macrophages caused by contact of human PBMC with lipopolysaccharide.

(10) A method for prevention and/or therapy of progressive tubulointerstitial lesion after renal damage, lesion of exocrine, acinar and ductal interstitial tissues of pancreas or pancreatitis, and lesion of interstitial tissues of urinary tubule, which comprises using a pharmaceutical containing a compound suppressing the induction of effector macrophages caused by contact of human PBMC with mitomycin-treated human PBMC.

(11) A method for screening a compound which is able to prevent, mitigate or treat glomerular lesion of kidney, lesion of islet of Langerhans of pancreas or diabetes mellitus and diabetic glomerular lesion, which comprises measuring a suppressive action of a compound to be tested against the induction of effector macrophage caused by contact of human PBMC with lipopolysaccharide.

(12) The method for screening according to the above-mentioned (11), wherein effector macrophages are induced by incubation of human untreated PBMC in RPMI 1640 medium in the presence of a compound to be tested, lipopolysaccharide and human AB type serum, the said induced effector macrophages are brought into contact with monolayered autologous erythrocytes and a compound showing less production of SPFC, Spontaneous Plaque-Forming Cell, as compared with the absence of the said compound to be tested is screened.

(13) A method for screening a compound which is able to prevent, mitigate or treat progressive tubulointerstitial lesion after renal damage, lesion of exocrine acinar and ductal interstitial tissues of pancreas or pancreatitis and lesion of interstitial tissues of urinary tubule, which comprises measuring a suppressive action of a compound to be tested against the induction of effector macrophages caused by contact of human PBMC with mitomycin-treated human PBMC.

(14) The method for screening according to the above-mentioned (13), wherein effector macrophages are induced by a mixed incubation of mitomycin-treated human PBMC and human untreated PBMC in RPMI 1640 medium in the presence of a compound to be tested and human AB type serum, the said induced effector macrophages are brought into contact with monolayered autologous erythrocytes and a compound showing less production of SPFC as compared with the absence of the said compound to be tested is screened.

(15) A kit for screening a compound which is able to prevent, mitigate or treat glomerular lesion of kidney, lesion of islet of Langerhans of pancreas or diabetes mellitus and diabetic glomerular lesion, which comprises (a) human PBMC, (b) lipopolysaccharide, (c) human AB type serum, (d) RPMI 1640 medium and (e) a plate to which monolayered autologous erythrocytes are adhered.

(16) A kit for screening a compound which is able to prevent, mitigate or treat progressive tubulointerstitial lesion after renal damage, lesion of exocrine, acinar and ductal interstitial tissues of pancreas or pancreatitis and lesion of interstitial tissues of urinary tubule, which comprises (a) human PBMC, (b) mitomycin-treated human PBMC, (c) human AB type serum, (d) RPMI 1640 medium and (e) a plate to which monolayered autologous erythrocytes are adhered.

(17) A method for the induction of effector macrophages which are a cause of glomerular lesion of kidney, lesion of islets of Langerhans of pancreas or diabetes mellitus and diabetic glomerular lesion, which comprises bringing lipopolysaccharide into contact with human PBMC.

(18) A method for the induction of effector macrophages which are a cause of progressive tubulointerstitial lesion after renal damage, lesion of exocrine, acinar and ductal interstitial tissues of pancreas or pancreatitis and lesion of interstitial tissues of urinary tubule, which comprises bringing human PBMC into contact with mitomycin-treated human PBMC.

(19) The pharmaceutical according to any of the above-mentioned (1) to (8), which comprises a compound represented by the formula (1)

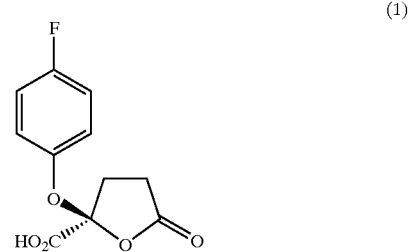

(1)

or a compound represented by the formula (2).

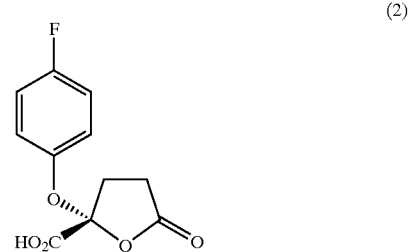

(2)

(20) An optical isomer γ-lactone represented by the formula (3)

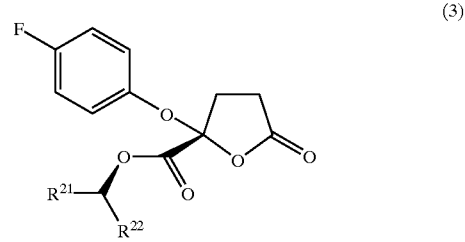

(3)

or by the formula (4)

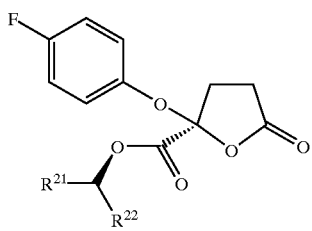
(4)

(in the formula, $R^{21}$ is an optionally substituted naphthyl group and $R^{22}$ is an optionally substituted straight or branched hydrocarbon group having 1 to 6 carbon atoms) or a mixture of the above optical isomers.

(21) The optical isomer γ-lactone or a mixture of the optical isomers according to the above-mentioned (20), wherein $R^{21}$ is naphthyl and $R^{22}$ is methyl.

(22) A compound represented by the formula (5) or a pharmacologically acceptable salt thereof.

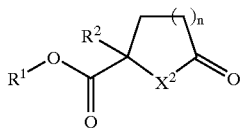
(5)

(in the formula, (a) $R^1$ and $R^2$ may be the same or different and each is hydrogen, an open-chain aliphatic hydrocarbon group which may be substituted or interrupted by an intervening group, an optionally substituted cyclic aliphatic hydrocarbon group, an optionally substituted aryl group, an optionally substituted heterocyclic group or an optionally substituted condensed heterocyclic group; $X^2$ is O, S or $NR^3$ in which $R^3$ is hydrogen, oxygen, an open-chain aliphatic hydrocarbon group which may be substituted or interrupted by an intervening group, an optionally substituted cyclic aliphatic hydrocarbon group, an optionally substituted aryl group, an optionally substituted heterocyclic group or an optionally substituted condensed heterocyclic group; and n is an integer from 1 to 5 or (b) $X^2$ is O, S or $NR^3$; $R^1$, $R^2$ and $R^3$ each is a substituent represented by the formula $R^{10}$—Z—$R^{11}$— (in which $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group); and n is an integer from 1 to 5).

(23) A compound represented by the formula (6) or a pharmacologically acceptable salt thereof.

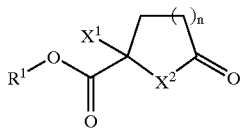
(6)

(in the formula, $R^1$, $X^2$ and n have the same meaning as defined in the above-mentioned (4); $X^1$ is halogen, cyano group, an optionally substituted mercapto group, an optionally substituted sulfo group, an optionally substituted sulfonyl group, an optionally substituted hydroxyl group, an optionally substituted amino group or an optionally substituted phosphoryl group).

(24) A compound represented by the formula (7) or a pharmacologically acceptable salt thereof.

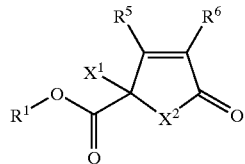
(7)

(in the formula, $R^1$ and $X^2$ have the same meaning as defined in the above-mentioned (4); $X^1$ has the same meaning as defined in the above-mentioned (5); $R^5$ and $R^6$ may be the same or different and each is (a) hydrogen, a straight or branched aliphatic hydrocarbon group which may be substituted or interrupted by an intervening group, an optionally substituted cyclic aliphatic hydrocarbon group, or an optionally substituted heterocyclic group, an optionally substituted condensed heterocyclic group, (b) a substituent represented by the formula $R^{10}$—Z—$R^{11}$— (in the formula, $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group.), or (c) $R^5$ and $R^6$ together with the carbon atom to which they are attached form an optionally substituted aromatic ring).

(25) The pharmaceutical according to any of the above-mentioned (1) to (8), which comprises a compound mentioned in any of the above-mentioned (20) to (24).

(26) An immunosuppressant or a fibrosis inhibitor which comprises a compound mentioned in any of the above-mentioned (19) to (24).

(27) The pharmaceutical according to any of the above-mentioned (1) to (8), which comprises ethyl 2-ketoglutarate or benzyl 2-ketoglutarate.

BEST MODE FOR CARRYING OUT THE INVENTION (1) Firstly, the present invention provides a method for the induction of effector macrophage which is induced and activated corresponding to the lesion inherent to the tissues after the organic damage and results in progressive lesion after the organic damage.

Thus, the present invention provides (a) a method for the induction of effector macrophage which is a cause of glomerular lesion of kidney, lesion of islets of Langerhans of pancreas or diabetes mellitus and diabetic glomerular lesion, characterized in that, lipopolysaccharide is brought into contact with human PBMC (hereinafter, abbreviated as "LPS inducing method") and (b) a method for the induction of effector macrophage which is a cause of progressive tubulointerstitial lesion after renal damage, lesion of exocrine, acinar or ductal interstitial tissues of pancreas or pancreatitis and tubulointerstitial lesion, characterized in that, human PBMC are brought into contact with mitomycin-treated human PBMC (hereinafter, abbreviated as "allo-MLC inducing method").

Hereunder, an LPS inducing method will be illustrated in detail.

With regard to a lipopolysaccharide used for the LPS inducing method, that which has been known per se may be used. For example, the lipopolysaccharide derived from Gram-negative bacteria such as *Salmonella* and *Escherichia*

*coli* may be used. It may be either the so-called rough type or smooth type.

For the preparation of the lipopolysaccharide, a method which has been known per se may be used. An example is a method where it is extracted from microbe and, if desired, a treatment for removing the toxicity is conducted. Examples of the method for extracting from microbe are a method of extracting with hot phenol (Westphal & Jann., *Methods Carbohydr. Chem.*, 5, 83–99 (1965)) and a method where microbe is treated with proteinase K in the presence of sodium lauryl sulfate. In addition, chemically synthesized one may be used or the commercially available one may be appropriately used.

In the present invention, it is preferred that lipopolysaccharide is used as a solution and, when it is made into a solution using an appropriate solvent, preferably, RPMI 1640 liquid, it is preferred to use a solution of a high concentration of about 60 to 100 $\mu$g/ml, more preferably about 70 to 90 $\mu$m/ml or still more preferably about 80 $\mu$g/ml.

The human PBMC can be obtained from human peripheral blood by a method known per se. An example for a method for separating the mononuclear cells from human peripheral blood is a method by a centrifugal separation using Ficoll-Paque (registered trademark; manufactured by Pharmacia Fine Chemicals). To be more specific, the above-mentioned method comprises (a) a step where Ficoll-Paque is placed at the bottom of a test tube, (b) a step where a blood sample as it is or after being diluted is carefully transferred onto the Ficoll-Paque using a pipette, (c) a step where the blood preparation prepared by Ficoll-Paque in (b) is centrifuged at about 400~500 G for about 30~40 minutes so that a blood component having larger specific gravity than the specific gravity of Ficoll-Paque comes into Ficoll-Paque or passes Ficoll-Paque and (d) a step where the mononuclear cell layer separated on the upper area of Ficoll-Paque is collected.

A specific mode for the LPS inducing method is a method where human PBMC is incubated in RPMI 1640 medium in the presence of lipopolysaccharide and human AB type serum to induce the effector macrophage and that method is advantageously used in the present invention.

At that time, a combination of any two of or all of lipopolysaccharide, human AB type serum and human PBMC may be previously mixed and then added to the medium or each of them may be added to the medium solely. There is no limitation for the order of adding to the medium. More preferably however, human untreated PBMC are added to RPMI 1640 medium to which human AB type serum is previously added and then lipopolysaccharide is added thereto.

RPMI 1640 medium is mentioned in Goding, J. W. (1980) *J. Immunol. Methods*, 39, 185 and *JAMA*, 199 (1957), 519. Alternatively, a commercially available product (manufactured by Sigma) may be used as well.

More preferred mode for carrying out the LPS inducing method is as follows.

Human untreated PBMC are dissolved in a concentration of about 2×10$^6$ cells/ml to RPMI 1640 medium to which gentamicin, L-glutamine and human AB type serum are added to concentrations of about 5 $\mu$g/ml, about 2 mM and about 10% by weight, respectively and then lipopolysaccharide is added thereto so as to make its final concentration about 80 $\mu$g/ml to prepare a culture liquid. The said culture liquid is incubated at about 37° C. for about six days with about 5% of $CO_2$.

A method for the induction of allo-MLC will be mentioned in detail as follows.

The mitomycin-treated human PBMC used in an allo-MLC inducing method can be prepared, for example, by adding mitomycin to the human PBMC obtained by the above-mentioned known method to make the final concentration of mitomycin about 40 $\mu$g/ml followed by subjecting to a heating treatment at about 37° C. for about 30 minutes.

A specific mode for an allo-MLC inducing method is a method where mitomycin-treated human PBMC and normal human untreated PBMC are subjected to a mixed culture in RPMI 1640 medium in the presence of human AB type serum to induce the effector macrophage and that method is advantageously used in the present invention.

At that time, a combination of any two of or all of human AB type serum, mitomycin-treated human PBMC and human PBMC may be previously mixed and then added to the medium or each of them may be added to the medium solely. There is no limitation for the order of adding to the medium. It is preferred however that normal human untreated PBMC are added to RPMI 1640 medium to which human AB type serum is previously added and then mitomycin-treated human PBMC are added thereto.

A more preferred mode of carrying out the allo-MLC inducing method will be as follows.

Human untreated PBMC are dissolved in a concentration of about 2×10$^6$ cells/ml to RPMI 1640 medium to which gentamicin, L-glutamine and human AB type serum are added to concentrations of about 5 $\mu$g/ml, about 2 mM and about 10% by weight, respectively and then mitomycin-treated human PBMC are added thereto so as to make the final concentration of about 2×10$^6$ cells/ml to prepare a culture liquid. The said culture liquid is incubated at about 37° C. for about six days with about 5% of $CO_2$.

(2) The present invention then provides a method for screening a compound which is able to prevent, mitigate or treat the progressive lesion after organic damage by a selective suppression of induction of effector macrophage corresponding to lesion inherent to the tissues after organic damage.

Thus, the present invention provides a method for screening a compound which is able to prevent, mitigate or treat glomerular lesion of kidney, lesion of islets of Langerhans of pancreas or diabetes mellitus and diabetic glomerular lesion, characterized in that, a suppressive action of a compounded to be tested to the induction of effector macrophage caused by contact of human PBMC with lipopolysaccharide is measured.

Preferred embodiment of the above-mentioned screening method according to the present invention will be as follows.

First, human PBMC are brought into contact with lipopolysaccharide in the presence of the compound to be tested to induce effector macrophage. Then, measurement is carried out to check whether the compounded to be tested shows a suppressive action to induction of effector macrophage.

It is preferred that the above-mentioned induction of effector macrophage is carried out in the same manner as in the above-mentioned LPS inducing method except that, when lipopolysaccharide is brought into contact with human PBMC, the compound to be tested is further present.

It is preferred that the measurement of the above-mentioned suppressive action to the induction of effector macrophage is carried out by measuring the numbers of spontaneous plaque-forming cells (hereinafter, referred to as SPFC) which are produced by bringing the induced effector macrophage into contact with monolayered autologous erythrocytes. Thus, when the numbers of the produced SPFC are less than the case where no test compound to be tested is present, it is judged that induction of effector macrophage is suppressed.

More preferred embodiment will be as follows.

Human untreated PBMC are dissolved in a concentration of about $2\times10^6$ cells/ml to RPMI 1640 medium to which gentamicin, L-glutamine and human AB type serum are added to concentrations of about 5 µg/ml, about 2 mM and about 10% by weight, respectively and then lipopolysaccharide is added to the solution so as to make its final concentration of about 80 µg/ml.

A compound to be tested is dissolved in an appropriate solvent, preferably dimethyl sulfoxide (DMSO) of about 0.001% by weight and the resulting test solution is added to above-mentioned medium. At that time, there are prepared various media where concentrations of the compound to be tested are different. It is preferred that the concentrations of the compound to be tested are about 1 µM to 0.001 µM.

The mixture is incubated at about 37° C. for about six days in the presence of about 5% of $CO_2$ to induce effector macrophage. The effector macrophage generated in the cultured PBMC induced from the culture liquid is recovered. In the recovering, known methods may be used and, for example, there is a method where the adhered thing is recovered using a rubber-policeman (spatula made of rubber). After that, washing may be carried out. For the washing, it is preferred to use a Hanks solution to which gentamicin is added so as to make its concentration of about 5 µg/ml.

In the meanwhile, monolayered autologous erythrocytes are prepared. The monolayered autologous erythrocytes may be manufactured by methods known per se but the following method is preferred.

Autologous erythrocytes are made about 4% by weight concentration by a Hanks solution without serum supplementation. It is preferred to use the autologous erythrocytes which are prepared by the above-mentioned known method and preserved at about 4° C. in a phosphate-buffered physiological saline (hereinafter, referred to as PBS) with addition of 0.1% of AB serum. Poly-L-lysine is added to a Terasaki plate, treated at about 37° C. for about 20 minutes and washed with PBS, the above-mentioned autologous erythrocytes are added immediately thereafter and allowed to stand at about 37° C. for about 30 minutes and the erythrocytes which are not adhered are removed to give a Terasaki plate to which monolayered autologous erythrocytes are adhered.

The induced effector macrophage which is recovered hereinabove is dissolved/suspended in the Hanks solution with 5 µg/ml of gentamicin so as to make about $2\times10^6$ cells/ml. To the above Terasaki plate to which the monolayered autologous erythrocytes are adhered is added 1 to 10 µl of the Hanks solution, the above dissolved/suspended liquid is added thereto in the same amount and the mixture is allowed to stand at about 37° C. for about 2 hours. After completion of the reaction, it is preferred to fix by formalin. Numbers of the produced SPFC can be easily measured by a phase-contrast microscope.

With regard to an index for the suppression of induction of effector macrophage, it is preferred to use an $IC_{50}$ concentration. The $IC_{50}$ can be calculated as follows.

When plural experiments are carried out under the same conditions, a mean value of the SPFC production numbers measured as above is determined. Then, SPFC production numbers per $1\times10^6$ of induced macrophages are calculated and, from the recovered induced macrophage numbers, the produced SPFC numbers are determined (this value will be called S1). Effector macrophage is induced as above without addition of the compound to be tested and SPFC production numbers are measured by the same manner (this value will be called S2). Concentration of the substance to be tested when S1 becomes one half of S2 is defined as $IC_{50}$.

With regard to the compound which is able to prevent, mitigate or cure the progressive lesion after organic damage found by the screening method according to the present invention, the compound where $IC_{50}$ is 1 µM or less is preferred.

The present invention further provides a method for screening a compound which is able to prevent, mitigate or treat progressive tubulointerstitial lesion after renal damage, lesion of exocrine, acinar or ductal interstitial tissues of pancreas or pancreatitis, and lesion of tubulointerstitial tissues associated with pancreatitis, characterized in that, a suppressive action of a compounded to be tested to the induction of effector macrophage caused by contact of human PBMC with mitomycin-treated human PBMC is measured.

A preferred embodiment of the above-mentioned screening method according to the present invention is as follows. Firstly, human PBMC are brought into contact with mitomycin-treated human PBMC in the presence of a compound to be tested to induce effector macrophage. After that, a measurement is carried out to check whether the compound to be tested shows a suppressive action to the induction of effector macrophage.

It is preferred to induce the above effector macrophage in the same manner as in the case of inducing method for the above allo-MLC except that the compound to be tested is further present in bringing the human PBMC into contact with mitomycin-treated human PBMC. Concentration of the compound to be tested is preferably in about 1 µM to 0.001 µM the same as in the above screening method and it is preferred to conduct the induction of effector macrophage by adding the compounded to be tested in various concentrations.

It is preferred that the measurement of the suppressive action of the compound to be tested to induction of the above-mentioned effector macrophage is carried out by the same manner as in the above-mentioned screening method.

The above-mentioned compound to be tested may be anything and may be, for example, peptide, protein, non-peptidic compound, synthetic compound, fermented product, cell extract, vegetable extract, animal tissue extract and plasma. It may be either a known compound or a novel compound.

It is also possible to combine known methods in such a manner that plural compounds to be tested are screened at the same time and, only when a suppressive action to the induction of effector macrophage is detected, suppressive action for each compound is measured by the above-mentioned method and the compound having a suppressive action is identified, etc.

The present invention further provides a screening kit for carrying out the above-mentioned screening method. There is no particular limitation for the form of the said screening kit although the forms which have been known per se may be used.

For example, a preferred embodiment of a screening kit for screening a compound which is able to prevent, mitigate or treat glomerular lesion of kidney, lesion of islets of Langerhans of pancreas or diabetes mellitus and diabetic glomerular lesion is a kit which comprises (a) human PBMC, (b) lipopolysaccharide, (c) human AB type serum, (d) RPMI 1640 medium and (e) a plate to which monolayered autologous erythrocytes are adhered.

Preferred one is such a kit containing Hanks solution to which (a) a solution prepared by adding human PBMC and lipopolysaccharide are added to an extent of about $2 \times 10^6$/ml and about 80 μg/ml, respectively to RPMI 1640 containing about 5 μg/ml of gentamicin, about 2 mM of L-glutamine and about 10% by weight of human AB type serum, (b) a plate to which monolayered erythrocytes are adhered and (c) about 5 μg/ml of gentamicin are added.

A preferred embodiment of a screening kit for screening a compound which is able to prevent, mitigate or treat progressive tubulointerstitial lesion after renal damage, or lesion of exocrine, acinar or ductal interstitial tissues of pancreas is a kit comprising (a) human PBMC, (b) mitomycin-treated human PBMC, (c) human AB type serum, (d) RPMI 1640 medium and (e) a plate to which monolayered autologous erythrocytes are adhered.

Preferred one is the said kit containing a Hanks solution to which (a) a solution prepared by adding human PBMC and mitomycin-treated human PBMC to an extent of about $2 \times 10^6$/ml each to RPMI 1640 containing about 5 μg/ml of gentamicin, about 2 mM of L-glutamine and about 10% by weight of human AB type serum, (b) a plate to which monolayered erythrocytes are adhered and (c) about 5 μg/ml of gentamicin are added.

(3) The present invention provides a pharmaceutical for prevention or therapy of progressive lesion after organic damage by a selective suppression of induction of effector macrophage corresponding to the lesion inherent to the tissues after the organic damage and also provides a therapeutic method using the said pharmaceutical.

Thus, the present invention provides a pharmaceutical for prevention and/or therapy of glomerular lesion of kidney, lesion of islets of Langerhans of pancreas or diabetes mellitus or diabetic glomerular lesion, characterized in that, the pharmaceutical contains a compound which suppresses the induction of effector macrophage caused by contact of human PBMC with lipopolysaccharide.

The present invention also provides a pharmaceutical for prevention and/or therapy of progressive tubulointerstitial lesion after renal damage, lesion of exocrine, acinar or ductal interstitial tissues of pancreas and pancreatitis and lesion of tubulointerstitial tissues which is a complication of pancreatitis, characterized in that, the pharmaceutical contains a compound which suppresses the induction of effector macrophage caused by contact of human PBMC with mitomycin-treated human PBMC.

With regard to (a) a compound which suppresses the induction of effector macrophage caused by contact of human PBMC with lipopolysaccharide and (b) a compound which suppresses the induction of effector macrophage caused by contact of human PBMC with mitomycin-treated human PBMC, the compounds which show the suppression to the induction of effector macrophage by the above-mentioned screening methods may be exemplified.

When a compound which shows activity as a result of the screening is acidic or basic, a salt of such a compound may be used as the pharmaceutical as well. Salt of the said compound is a salt with a physiologically acceptable acid (such as inorganic acid and organic acid) or base (such as alkaline metal). To be more specific, there may be used inorganic acid salt such as a salt with hydrochloric acid, phosphoric acid, hydrobromic acid and sulfuric acid; organic acid salt such as a salt with acetic acid, formic acid, propionic acid, fumaric acid, maleic acid, succinic acid, tartaric acid, citric acid, malic acid, oxalic acid, benzoic acid, methanesulfonic acid and benzenesulfonic acid; inorganic base salt such as sodium salt, potassium salt and ammonium salt; and organic base salt such as dimethylamine salt and cyclohexylamine salt.

The compound which is used for a pharmaceutical or a therapeutic method according to the present invention may be a prodrug or a derivative of the above-mentioned compound as well.

With regard to the compound used as a pharmaceutical according to the present invention, the following compounds may be specifically exemplified.

Specific examples of the compound which are able to prevent, mitigate or cure glomerular lesion of the kidney, lesion of islet of Langerhans of pancreas or diabetes mellitus or diabetic glomerular lesion by suppressing the induction of effector macrophage caused by contact of human PMBC with lipopolysaccharide are the following compounds (6-1, (6-2) and (3-2).

Specific examples of the compounds which are able to prevent, mitigate or cure progressive tubulointerstitial lesion after renal damage, lesion of exocrine, acinar or ductal interstitial tissues of pancreas and pancreatitis and lesion of tubulointerstitial tissues which is a complication of pancreatitis by suppressing the induction of effector macrophage caused by contact of human PMBC with mitomycin-treated PMBC are the following compounds (9-1), (7-3), (7-5) and (4-2).

With regard to the above-mentioned compounds, there are a compound represented by the formula (1)

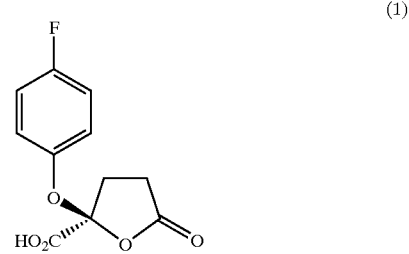

(1)

and a compound represented by the formula (2).

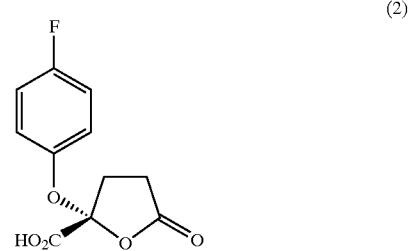

(2)

There is also an optical isomer γ-lactone represented by the formula (3)

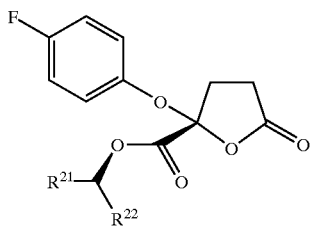
(3)

or by the formula (4)

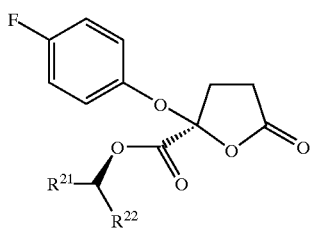
(4)

(in the formulae, $R^{21}$ is an optionally substituted naphthyl and $R^{22}$ is an optionally substituted open-chain hydrocarbon group having 1 to 6 carbons) and a mixture of such optical isomers.

Among them, the compound where $R^{21}$ is naphthyl group and $R^{22}$ is methyl group is preferred.

There is also a compound represented by the formula (5) and a pharmacologically acceptable salt thereof.

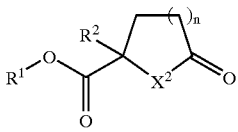
(5)

(in the formula, (a) $R^1$ and $R^2$ may be the same or different and each is hydrogen, an open-chain aliphatic hydrocarbon group which may be substituted or interrupted by an intervening group, an optionally substituted cyclic aliphatic hydrocarbon group, an optionally substituted aryl group, an optionally substituted heterocyclic group or an optionally substituted condensed heterocyclic group; $X^2$ is O, S or $NR^3$ in which $R^3$ is hydrogen, oxygen, an open-chain aliphatic hydrocarbon group which may be substituted or interrupted by an intervening group, an optionally substituted cyclic aliphatic hydrocarbon group, an optionally substituted aryl group, an optionally substituted heterocyclic group or an optionally substituted condensed heterocyclic group; and n is an integer from 1 to 5 or (b) $X^2$ is O, S or $NR^3$; $R^1$, $R^2$ and $R^3$ each is a substituent represented by the formula $R^{10}$—Z—$R^{11}$— (in which $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group); and n is an integer from 1 to 5).

There is further a compound represented by the formula (6) or a pharmacologically acceptable salt thereof.

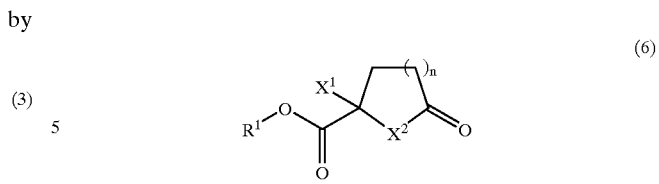
(6)

(in the formula, $R^1$, $X^2$ and n have the same meaning as defined in the above-mentioned item(4); $X^1$ is halogen, cyano group, an optionally substituted mercapto group, an optionally substituted sulfo group, an optionally substituted sulfonyl group, an optionally substituted hydroxyl group, an optionally substituted amino group or an optionally substituted phosphoryl group).

There is still further a compound represented by the formula (7) or a pharmacologically acceptable salt thereof.

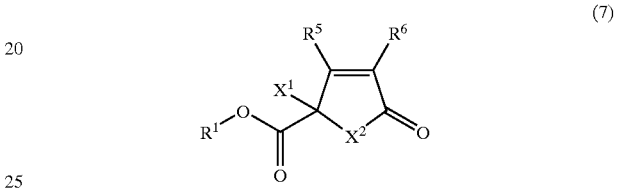
(7)

(in the formula, $R^1$ and $X^2$ have the same meaning as defined in the above-mentioned item (4); $X^1$ has the same meaning as defined in the above-mentioned item(5); $R^5$ and $R^6$ may be the same or different and each is (a) hydrogen, an open-chain aliphatic hydrocarbon group which may be substituted or interrupted by an intervening group, an optionally substituted cyclic aliphatic hydrocarbon group, an optionally substituted heterocyclic group or an optionally substituted condensed heterocyclic group, (b) a substituent represented by the formula $R^{10}$—Z—$R^{11}$— (in the formula, $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group.), or (c) $R^5$ and $R^6$ is an optionally substituted aromatic ring together with the carbon atom to which they are attached).

In the compound represented by the formula (3) or (4), $R^{21}$ is an optionally substituted naphthyl group.

Examples of the substituent are halogen (preferably, fluorine, chlorine and bromine), an oxo group, an alkanoyl group (preferably $C_{1-8}$), an alkanoyloxy group (preferably $C_{1-8}$), an alkanoylamino group (preferably $C_{1-8}$), carboxyl group, an alkoxycarbonyl group (preferably $C_{2-8}$), a haloalkylcarbonyl group (preferably $C_{2-8}$), an alkoxy group (preferably $C_{1-8}$), a haloalkoxy group (preferably $C_{1-8}$), amino group, an alkylamino group (preferably $C_{1-8}$), a dialkylamino group (preferably $C_{2-16}$), a cyclic amino group, an alkylaminocarbonyl group (preferably $C_{2-8}$), carbamoyl group, hydroxyl group, nitro group, cyano group, mercapto group, an alkylthio group (preferably $C_{1-8}$), an alkylsulfonyloxy group (preferably $C_{1-8}$), an alkylsulfonylamino group (preferably $C_{1-8}$) and phenyl group.

Further, the naphtyl group may be substituted by such group(s) at one or more position(s).

The naphthyl group represented by a substituent $R^{21}$ may also be substituted with open-chain or cyclic hydrocarbon group which will be mentioned later in detail. Carbon number(s) of the hydrocarbon group is/are preferably 1 to 8. The said open-chain or cyclic hydrocarbon group may be substituted, for example, with halogen, hydroxyl group, amino group, nitro group, cyano group, mercapto group, carbamoyl group, alkanoyl group, alkanoyloxy group or alkanoylamino group.

The open-chain hydrocarbon group as a substituent for naphthyl group may be interrupted by an intervening group such as —O—, —CO—, —COO—, —S—, —SO—, —$SO_2$—, —NH—, —$NR^3$—, —NH—CO—, —$NR^3$—CO—, —NH—$SO_2$—, —$NR^3$—$SO_2$—, —Si— or phosphoryl group.

The substituent $R^3$ is (a) hydrogen, oxygen, an open-chain hydrocarbon residue which may be substituted or interrupted by an intervening group, an optionally substituted cyclic aliphatic hydrocarbon group, an optionally substituted aryl group, an optionally substituted heterocyclic group or an optionally substituted condensed heterocyclic group or (b) a substituent represented by the formula $R^{10}$—Z—$R^{11}$— (in which $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group).

The naphthyl group represented by the substituent $R^{21}$ may be substituted with a substituent represented by $R^{10}$—Z—$R^{11}$— (in the formula, $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group).

In the compound represented by the formula (3) or (4), $R^{22}$ is an optionally substituted open-chain hydrocarbon group having 1 to 6 carbon(s).

The term "open-chain hydrocarbon group having 1 to 6 carbon(s)" means that carbon number(s) therein is/are 1 to 6 and it may be either straight or branched and either saturated or unsaturated.

Its examples are methyl group, ethyl group, propyl group, isopropyl group, n-butyl group, isobutyl group, tert-butyl group, n-pentyl group, isopentyl group, tert-pentyl group and n-hexyl group.

Examples of the substituent in the open-chain hydrocarbon group are halogen, hydroxyl group, amino group, nitro group, cyano group, mercapto group, carbamoyl group, alkanoyl group, alkanoyloxy group and alkanoylamino group.

In the compounds represented by the formulae (5) to (7), the substituents $R^1$ and $R^2$ may be the same or different and each is (a) hydrogen, an open-chain aliphatic hydrocarbon group which may be substituted or interrupted by an intervening group, an optionally substituted cyclic aliphatic hydrocarbon group, an optionally substituted aryl group, an optionally substituted heterocyclic group or an optionally substituted condensed heterocyclic group or (b) a substituent represented by the formula $R^{10}$—Z—$R^{11}$— (in which $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group).

The term "open-chain aliphatic hydrocarbon group" in the substituents $R^1$ and $R^2$ may be straight or branched and may be saturated or unsaturated.

To be more specific, there may be exemplified an alkyl group such as methyl group, ethyl group, n-propyl group, isopropyl group, n-butyl group, isobutyl group, tert-butyl group, n-pentyl group, isopentyl group, tert-pentyl group, n-hexyl group, 1,1-dimethylpropyl group and 3-methyl-3-butenyl group; an alkenyl group such as vinyl group, allyl group, 1-propenyl group, isopropenyl group, 2-butenyl group, 1,3-butadienyl group and 2-pentenyl group; and an alkynyl group such as ethynyl group, 2-propynyl group, 1-butynyl group and 2-butynyl group.

It is also possible that both double bond and triple bond are present in one substituent such as 2-penten-4-ynyl.

Carbon number(s) is/are preferably 1 to 8. Especially for the substituent $R^2$, ethynyl group or 2-propynyl group are preferred.

The "cyclic aliphatic hydrocarbon group" in the substituent $R^1$ and $R^2$ may be saturated or unsaturated or may be cross-linked.

To be more specific, there may be exemplified a cycloalkyl group such as cyclopropyl group, cyclobutyl group, cyclopentyl group, cyclohexyl group, cycloheptyl group, adamantyl group and bicyclo[2.2.1]heptyl group; and a cycloalkenyl group such as 2-cyclopenten-1-yl group and 2,4-cyclopentadien-1-yl group.

Carbon numbers of the cyclic aliphatic hydrocarbon group are preferably 3 to 12.

The open-chain or cyclic aliphatic hydrocarbon group in the substituents $R^1$ and $R^2$ may be substituted with the substituent which will be mentioned later. With regard to the position of such a substituent, there is no particular limitation so far as it is chemically allowed.

The open-chain hydrocarbon group as a substituent in the substituents $R^1$ and $R^2$ may be interrupted by an intervening group such as —O—, —CO—, —COO—, —S—, —SO—, —$SO_2$—, —NH—, —$NR^3$—, —NH—CO—, —$NR^3$—CO—, —NH—$SO_2$—, —$NR^3$—$SO_2$—, —Si— or phosphoryl group. $R^3$ is (a) hydrogen, oxygen, an open-chain hydrocarbon residue which may be substituted or interrupted by an intervening group, an optionally substituted cyclic aliphatic hydrocarbon group, an optionally substituted aryl group, an optionally substituted heterocyclic group or an optionally substituted condensed heterocyclic group or (b) a substituent represented by the formula $R^{10}$—Z—$R^{11}$— (in which $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group).

The "aryl group" in the substituents $R^1$ and $R^2$ is an aromatic hydrocarbon group which may be partially saturated and there may be exemplified phenyl group, benzyl group, biphenyl group, indenyl group and naphthyl group or a partially saturated group thereof such as 2,3-dihydroindenyl group and 1,2,3,4-tetrahydronaphthyl group.

Preferred carbon numbers of the aryl group are 6 to 20.

Such an aryl group may be substituted with the substituent which will be mentioned later and, with regard to the position of the linkage and the position of the substituent, there is no particular limitation so far as they are chemically allowed.

With regard to the substituent $R^1$ and $R^2$, benzyl group is preferred and, with regard to the substituent $R^2$, it is also preferred that 4-position is substituted with fluorine.

With regard to the "heterocyclic group" in the substituent $R^1$ and $R^2$, there may be exemplified five- to six-membered saturated or unsaturated ring containing 1 to 3 hetero atom (s) selected from nitrogen atom, oxygen atom and sulfur atoms in a ring.

Examples of such a heterocyclic group are an aromatic heterocyclic group such as pyrrolyl group, furyl group, thienyl group, imidazolyl group, oxazolyl group, thiazolyl group, pyrazolyl group, isoxazolyl group, isothiazolyl group, oxadiazolyl group, triazolyl group, indolyl group, benzofuryl group, benzothienyl group, benzimidazolyl group, benzoxazolyl group, benzothiazolyl group, pyridyl group, pyrimidinyl group, pyrazinyl group, pyridazinyl group, triazolyl group, tetrazolyl group, quinolyl group and isoquinolyl group; a partially saturated heterocyclic group such as pyranyl group, 1,2-dihydroquinolyl group, 1,2,3,4-tetrahydroquinolyl group, 1,2-dihydroisoquinolyl group, 1,2,3,4-tetrahydroisoquinolyl group, dihydrofuryl group and dihydrothienyl group; and a saturated heterocyclic group such as pyrrolidinyl group, piperidinyl group, piperazinyl group, morpholinyl group, tetrahydrofuryl group and tetrahydrothienyl group.

Such a heterocyclic group may be substituted with the substituent which will be mentioned later and, with regard to the position of the linkage and the position of the substituent, there is no particular limitation so far as they are chemically allowed.

With regard to the "condensed heterocyclic group" in the substituent $R^1$ and $R^2$, there may be exemplified a case where a five- to six-membered saturated, partially saturated or unsaturated ring containing 1 to 3 hetero atom(s) selected from nitrogen atom, oxygen atom and sulfur atom in the ring is condensed with a benzene ring or other heterocyclic ring.

With regard to the condensed heterocyclic ring, there may be exemplified indole, 3H-indole, isoindole, benzofuran, benzothiophene, 1H-indazole, benzimidazole, benzoxazole, benzothiazole, benzisodxazole, benzisothiazole, quinoline, isoquinoline, quinazoline, 1,2-dihydroquinoline, 1,2,3,4-tetrahydroquinoline, 1,2-dihydroisoquinoline and 1,2,3,4-tetrahydroisoquinoline.

Such a condensed heterocyclic group may be substituted with the substituent which will be mentioned later. With regard to the position of the linkage and the position of the substituent in case substituent is present, there is no particular limitation so far as they are chemically allowed.

The substituents $R^1$ and $R^2$ may be a substituent represented by the formula $R^{10}$—Z—$R^{11}$—.

$R^{10}$ and $R^{11}$ may be the same or different and each is an optionally substituted open-chain or cyclic hydrocarbon group, an optionally substituted aryl group, an optionally substituted heterocyclic group or an optionally substituted condensed hetero group. With regard to the substituent, there may be exemplified a substituent which will be mentioned later.

With regard to the "substituent" in the open-chain or cyclic aliphatic hydrocarbon group, the aryl group, the heterocyclic group or the condensed heterocyclic group, a substituent which is conventionally used in the field of pharmaceuticals may be used.

Examples of the substituent are halogen (preferably, fluorine, chlorine and bromine), an oxo group, an alkanoyl group (preferably $C_{1-8}$), an alkanoyloxy group (preferably $C_{1-8}$), an alkanoylamino group (preferably $C_{1-8}$), carboxyl group, an alkoxycarbonyl group (preferably $C_{2-8}$), a haloalkylcarbonyl group (preferably $C_{2-8}$), an alkoxy group (preferably $C_{1-8}$), a haloalkoxy group (preferably $C_{1-8}$), an alkyl group (preferably $C_{1-20}$), amino group, an alkylamino group (preferably $C_{1-8}$), a dialkylamino group (preferably $C_{2-16}$), a cyclic amino group, an alkylaminocarbonyl group (preferably $C_{2-8}$), carbamoyl group, hydroxyl group, nitro group, cyano group, mercapto group, an alkylthio group (preferably $C_{1-8}$), an alkylsulfonyloxy group (preferably $C_{1-8}$), an alkylsulfonylamino group (preferably $C_{1-8}$) and phenyl group.

Further, the group may be substituted by such group(s) at one or more position(s).

The substituent $X^2$ is O, S, NH or $NR^3$. Here, the substituent $R^3$ has the same meaning as defined above.

n is an integer of 1 to 5 and, preferably, it is 1.

The substituent $X^1$ is (a) halogen, (b) cyano group, (c) an optionally substituted mercapto group, an optionally substituted sulfo group or an optionally substituted sulfonyl group, (d) an optionally substituted hydroxyl group, (e) an optionally substituted amino group or (f) an optionally substituted phosphoryl group.

Examples of the substituent are halogen (preferably, fluorine, chlorine and bromine), an oxo group, an alkanoyl group (preferably $C_{1-8}$), an alkanoyloxy group (preferably $C_{1-8}$), an alkanoylamino group (preferably $C_{1-8}$), carboxyl group, an alkoxycarbonyl group (preferably $C_{2-8}$), a haloalkylcarbonyl group (preferably $C_{2-8}$), an alkoxy group (preferably $C_{1-8}$), a haloalkoxy group (preferably $C_{1-8}$), an alkyl group (preferably $C_{1-20}$), amino group, an alkylamino group (preferably $C_{1-8}$), a dialkylamino group (preferably $C_{2-16}$), a cyclic amino group, an alkylaminocarbonyl group (preferably $C_{2-8}$), carbamoyl group, hydroxyl group, nitro group, cyano group, mercapto group, an alkylthio group (preferably $C_{1-8}$), an alkylsulfonyloxy group (preferably $C_{1-8}$), an alkylsulfonylamino group (preferably $C_{1-8}$) and phenyl group.

Further, the group may be substituted by such group(s) at one or more position(s), if chemically acceptable.

With regard to the above-mentioned optionally substituted mercapto group, optionally substituted sulfo group or optionally substituted sulfonyl group, there may be exemplified benzoylthio group, tosyl group, phenylsulfo group and phenylsulfinyl group.

With regard to the above-mentioned optionally substituted hydroxyl group, there may be exemplified methoxy, ethoxy, propionyloxy, allyloxy, benzoxy and naphthoxy.

With regard to the above-mentioned optionally substituted amino group, there may be exemplified methylamino group, ethylamino group, anilino group and anisidino group.

With regard to the above-mentioned optionally substituted phosphoryl group, a substituent represented by the formula (9)

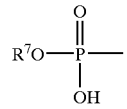

or by the formula (10)

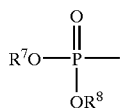

(in the formulae, substituents $R^7$ and $R^8$ may be the same or different and each is an optionally substituted open-chain or cyclic hydrocarbon group, an optionally substituted aryl group, an optionally substituted heterocyclic group or an optionally substituted condensed hetero group) is preferred. There may be exemplified methylphosphoryl group, dimethylphosphoryl group and methylethylphosphoryl group. Carbon number(s) of the said phosphoryl group is/are preferably 1 to 20.

In the compound (7), the substituents $R^5$ and $R^6$ each is (a) hydrogen, an open-chain hydrocarbon residue which may be substituted or interrupted by an intervening group, an optionally substituted cyclic aliphatic hydrocarbon group, an optionally substituted aryl group, an optionally substituted heterocyclic group or an optionally substituted condensed heterocyclic group or is (b) a substituent represented by the formula $R^{10}$—Z—$R^{11}$— (in which $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group).

To be specific, the above is the same description as that for the substituents $R^1$ and $R^2$.

The substituents $R^5$ and $R^6$ may be the same or different.

The substituents $R^5$ and $R^6$ may also form an aromatic ring together with a carbon to which they are bonded. There are exemplified the cases where benzene, naphthalene or indene is formed.

The said aromatic ring may be substituted. In that case, one or more position(s) may be substituted. Examples of the substituent are halogen (preferably, fluorine, chlorine and bromine), an oxo group, an alkanoyl group (preferably $C_{1-8}$), an alkanoyloxy group (preferably $C_{1-8}$), an alkanoylamino group (preferably $C_{1-8}$), carboxyl group, an alkoxycarbonyl group (preferably $C_{2-8}$), a haloalkylcarbonyl group (preferably $C_{2-8}$), an alkoxy group (preferably $C_{1-8}$), a haloalkoxy group (preferably $C_{1-8}$), an alkyl group (preferably $C_{1-20}$), amino group, an alkylamino group (preferably $C_{1-8}$), a dialkylamino group (preferably $C_{2-16}$), a cyclic amino group, an alkylaminocarbonyl group (preferably $C_{2-8}$), carbamoyl group, hydroxyl group, nitro group, cyano group, mercapto group, an alkylthio group (preferably $C_{1-8}$), an alkylsulfonyloxy group (preferably $C_{1-8}$), an alkylsulfonylamino group (preferably $C_{1-8}$) and phenyl group.

Further, the said aromatic ring may be substituted with the above-mentioned optionally substituted open-chain or cyclic hydrocarbon group. Preferably, carbon number(s) of the hydrocarbon group is/are 1 to 8. The said open-chain hydrocarbon group may be interrupted by an intervening group such as —O—, —CO—, —COO—, —S—, —SO—, —SO$_2$—, —NH—, —NR$^3$—, —NH—CO—, —NR$^3$—CO—, —NH—SO$_2$—, —NR$^3$—SO$_2$—, —Si— or phosphoryl group (where $R^3$ has the same meaning as the above-mentioned definition).

Still further, the said aromatic ring may be substituted with a substituent represented by the formula $R^{10}$—Z—$R^{11}$— (in the formula, $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocycylic group; and Z is an intervening group).

The compounds represented by the formulae (5) to (7) have an asymmetric carbon atom and, therefore, two optical isomers can exist. Accordingly, the pharmaceutical according to the present invention may contain one of the optical isomers only or may contain a racemate.

There is no particular limitation for the pharmacologically acceptable salts of the compounds represented by the formulae (5) to (7) and, to be more specific, there may be exemplified inorganic acid salt such as a salt with hydrochloric acid, phosphoric acid, hydrobromic acid and sulfuric acid; organic acid salt such as a salt with acetic acid, formic acid, propionic acid, fumaric acid, maleic acid, succinic acid, tartaric acid, citric acid, malic acid, oxalic acid, benzoic acid, methanesulfonic acid and benzenesulfonic acid; inorganic base salt such as sodium salt, potassium salt and ammonium salt; and organic base salt such as dimethylamine salt and cyclohexylamine salt.

With regard to the specific examples of the above-mentioned substituents in the present invention, the following substituents may be exemplified.

With regard to the above "alkanoyl group", there may be exemplified formyl group, acetyl group, propionyl group, butyryl group and pivaloyl group.

With regard to the above "alkanoyloxy group", there may be exemplified formyloxy group, acetoxy group, propionyloxy group, butyryloxy group and pivaloyloxy group.

With regard to the above "alkanoylamino group", there may be exemplified acetylamino group, propionylamino group, butyrylamino group and pivaloylamino group.

With regard to the above "alkoxycarbonyl group", there may be exemplified methoxycarbonyl group, ethoxycarbonyl group, propoxycarbonyl group, isopropoxycarbonyl group, butoxycarbonyl group, isobutoxycarbonyl group, tert-butoxycarbonyl group and pentyloxycarbonyl group.

With regard to the above "haloalkylcarbonyl group", there may be exemplified fluoroacetyl group, difluoroacetyl group, trifluoroacetyl group, chloroacetyl group, dichloroacetyl group, trichloroacetyl group, bromoacetyl group, dibromoacetyl group, tribromoacetyl group, 3-chloropropionyl group and 4-chlorobutyryl group.

The above "alkoxy group" means a straight or branched alkoxy group and there may be exemplified methoxy group, ethoxy group, propoxy group, isopropoxy group, butoxy group, tert-butoxy group, pentyloxy group, tert-pentyloxy group and hexyloxy group.

The above "haloalkoxy group" means a group where halogen atom is substituted in the above "alkoxy group" and there may be exemplified fluoromethoxy group, difluoromethoxy group, trifluoromethoxy group, chloromethoxy group, dichloromethoxy group, trichloromethoxy group, bromomethoxy group, dibromomethoxy group, tribromomethoxy group, iodomethoxy group, diiodomethoxy group, triiodomethoxy group, 2-fluoroethoxy group, 2,2-difluoroethoxy group, 2,2,2-trifluoroethoxy group, 2-chloroethoxy group, 2,2-dichloroethoxy group, 2,2,2-trichloroethoxy group, 2-bromoethoxy group, 2,2-dibromoethoxy group, 2,2,2-tribromoethoxy group, 3-chloropropoxy group and 4-chlorobutoxy group.

The above "alkylamino group" means a group where an amino group is substituted with an alkyl group and there may be exemplified methylamino group, propylamino group, isopropylamino group, butylamino group, isobutylamino group, tert-butylamino group, pentylamino group, isopentylamino group, tert-pentylamino group and hexylamine group.

The above "dialkylamino group" means a group where an amino group is disubstituted with an alkyl group in which the types of the alkyl groups may be the same or different and there may be exemplified dimethylamino group, ethylmethylamino group, diethylamino group, methylpropylamino group, ethylpropylamino group, dipropylamino group, diisopropylamino group, dibutylamino group, diisobutylamino group, di-tert-butylamino group, dipentylamino group, dilsopentylamino group, di-tert-pentylamino group and dihexylamino group.

The above "cyclic amino group" means a group where an amino group is in a cyclic form where four- to eight-membered cyclic amino groups are preferred and there may be exemplified azetidinyl group, pyrrolidinyl group and piperidino group as well as those having oxygen atom, sulfur atom or nitrogen atom as a hetero atom such as morpholino group, thiomorpholino group and piperazinyl group. The nitrogen atom of 4-position of the piperazinyl group may bear a substituent such as a lower alkyl group or an aryl group.

The above "alkylaminocarbonyl group" means a group where the "alkylamino" moiety is the already-mentioned "alkylamino group" and there may be exemplified methylaminocarbonyl group, ethylaminocarbonyl group, propylaminocarbonyl group, isopropylaminocarbonyl group, butylaminocarbonyl group, isobutylaminocarbonyl group, tert-butylaminocarbonyl group, pentylaminocarbonyl group, isopentylaminocarbonyl group, tert-pentylaminocarbonyl group and hexylaminocarbonyl group.

The above "alkylthio group" means a straight or branched alkylthio group and there may be exemplified methylthio group, ethylthio group, propylthio group, isopropylthio group, butylthio group, tert-butylthio group, pentylthio group, tert-pentylthio group and hexylthio group.

The above "alkylsulfonyloxy group" means a straight or branched alylsulfonyloxy group, and there may be exemplified methylsulfonyloxy group, ethylsulfonyloxy group, propylsulfonyloxy group, isopropylsulfonyloxy group, butylsulfonyloxy group, tert-butylsulfonyloxy group, pentylsulfonyloxy group, tert-pentylsulfonyloxy group and hexylsulfonyloxy group.

The above "alkylsulfonylamino group" means a group where an amino group is substituted with a straight or branched alkylsulfonyl group and there may be exemplified methylsulfonylamino group, ethylsulfonylamino group, propylsulfonylamino group, isopropylsulfonylamino group, butylsulfonylamino group, tert-butylsulfonylamino group, pentylsulfonylamino group, tert-pentylsulfonylamino group and hexylsulfonylamino group.

In a substituent represented by the formula $R^{10}$—Z—$R^{11}$— (in the formula, $R^{10}$ and $R^{11}$ may be the same or different and each is an optionally substituted open-chain or cyclic hydrocarbon group, aryl group, heterocyclic group or condensed heterocyclic group; and Z is an intervening group), examples of the intervening group are —O—, —CO—, —COO—, —S—, —SO—, —$SO_2$—, —NH—, —$NR^3$—, —NH—CO—, —$NR^3$—CO—, —NH—$SO_2$—, —$NR^3$—$SO_2$—, —Si— are phosphoryl group where $R^3$ has the same meaning as the above-mentioned definition.

With regard to the above-mentioned substituent, specific examples thereof are the following substituents.

(a) With regard to a substituent where the intervening group is —O—, there may be exemplified methoxymethyl group, ethoxymethyl group, ethoxyethyl group, propoxymethyl group, propoxyethyl group, isopropoxymethyl group, butoxymethyl group, butoxyethyl group, butoxypropyl group, tert-butoxymethyl group, tert-butoxyethyl group, pentyloxymethyl group, pentyloxyethyl group, pentyloxypropyl group, pentyloxybutyl group, tert-pentyloxymethyl group, tert-pentyloxyethyl group, hexyloxymethyl group, hexyloxyethyl group, hexyloxypropyl group, hexyloxypropyl group, benzyloxymethyl group and phenoxymethyl group.

Preferred carbon number(s) of the said substituent is/are 1 to 10.

(b) With regard to a substituent where the intervening group is —CO—, there may be exemplified acetylmethyl group, acetylethyl group, acetylpropyl group, acetylbutyl group, acetylpentyl group, acetylhexyl group, propionylmethyl group, butyrylmethyl group, isobutyrylmethyl group, valerylmethyl group, isovalerylmethyl group, hexanoylmethyl group and phenylacetylmethyl group.

Preferred carbon number(s) of the said substituent is/are 1 to 10.

(c) With regard to a substituent where the intervening group is —COO—, there may be exemplified acetoxymethyl group, acetoxyethyl group, acetoxypropyl group, acetoxybutyl group, acetoxypentyl group, acetoxyhexyl group, propionyloxymethyl group, tert-butyloxycarbonylmethyl group, 1-isobutyryloxyethyl group, 1-cyclohexyloxycarbonylethyl group, benzyloxycarbonylmethyl group, phenoxycarbonylmethyl group and pivaloyloxymethyl group.

Preferred carbon number(s) of the said substituent is/are 1 to 10.

(d) With regard to a substituent where the intervening group is —S—, there may be exemplified methylthiomethyl group, methylthioethyl group, methylthiopropyl group, methylthiobutyl group, methylthioheptyl group, methylthiohexyl group, methylthioisobutyl group, ethylthiomethyl group, propylthiomethyl group, butylthiomethyl group, heptylthiomethyl group, hexylthiomethyl group, benzylthiomethyl group and phenylthiomethyl group.

Preferred carbon number(s) of the said substituent is/are 1 to 10.

(e) With regard to a substituent where the intervening group is —$SO_2$—, there may be exemplified methylsulfonylmethyl group, methylsulfonylethyl group, methylsulfonylpropyl group, methylsulfonylbutyl group, methylosulfonylheptyl group, methylsulfonylhexyl group, methylsulfonylisobutyl group, ethylsulfonylmethyl group, propylsulfonylmethyl group, butylsulfonylmethyl group, heptylsulfonylmethyl group, hexylsulfonylmethyl group, benzylsulfonylmethyl group and phenylsulfonylmethyl group.

Preferred carbon number(s) of the said substituent is/are 1 to 10.

(f) With regard to a substituent where the intervening group is —SO—, there may be exemplified methylsulfinylmethyl group, methylsulfinylethyl group, methylsulfinylpropyl group, methylsulfinylbutyl group, methylsulfinylheptyl group, methylsulfinylhexyl group, methylsulfinylisobutyl group, ethylsulfinylmethyl group, propylsulfinylmethyl group, butylsulfinylmethyl group, heptylsulfinylmethyl group, hexylsulfinylmerhyl group, benzylsulfinylmethyl group and phenylsulfinylmethyl group.

Preferred carbon number(s) of the said substituent is/are 1 to 10.

(g) The substituent where the intervening group is —NH— is a compound represented by the formula $R^{10}$—NH—$R^{11}$— where $R^{11}$ is an optionally substituted open-chain or cyclic hydrocarbon group, an optionally substituted aryl group, an optionally substituted heterocyclic group and an optionally substituted condensed heterocyclic group as mentioned already. Examples of $R^{10}$—NH— are methylamino group, ethylamino group, propylamino group, isopropylamino group, butylamino group, isobutylamino group, tert-butylamino group, pentylamino group, isopentylamino group, tert-pentylamino group, hexylamino group, anilino group and benzylamino group.

Preferred carbon number(s) of the said substituent is/are 1 to 10.

(h) The substituent where the intervening group is —$NR^3$— is a compound represented by the formula $R^{10}$—$NR^3$—$R^{11}$— where $R^{11}$ is an optionally substituted open-chain or cyclic hydrocarbon group, an optionally substituted aryl group, an optionally substituted heterocyclic group and an optionally substituted condensed heterocyclic group as mentioned already.

Examples of $R^{10}$—$NR^3$— are dimethylamino group, ethylmethylamino group, diethylamino group, methylpropylamino group, ethylpropylamino group, dipropylamino group, diisopropylamino group, dibutylamino group, diisobutylamino group, di-tert-butylamino group, dipentylamino group, diisopentylamino group, di-tert-pentylamino group, dihexylamino group, dibenzylamino group and methylbenzylamino group.

The substituent $R^3$ has the same meaning as the above-mentioned definition.

Preferred carbon number(s) of the said substituent is/are 1 to 10.

(i) With regard to the substituent where the intervening group is —NH—CO—, —$NR^3$—CO—, NH—$SO_2$— or —$NR^3$—$SO_2$—, there may be exemplified a compound where an intervening group is changed to the above-mentioned one in the above-mentioned compound where the intervening group Z is —NH— or —$NR^3$—.

(j) With regard to the substituent where the intervening group Z is —Si—, there may be exemplified methylsilylmethyl group, methylsilylethyl group, methylsilylpropyl group, methylsilylbutyl group, methylsilylheptyl group, methylsilylhexyl group, methylsilylisobutyl group, ethylsilylmethyl group, propylsilylmethyl group, butylsilylmethyl group, heptylsilylmethyl group, hexylsilylmethyl group, benzylsilylmethyl group and phenylsilylmethyl group.

(k) The substituent where the intervening group Z is a phosphoryl group is represented by the formulae;

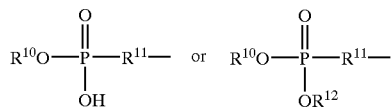

(in the formulae, the substituents $R^{10}$, $R^{11}$ and $R^{12}$ may be the same or different and each is an optionally substituted open-chain or cyclic hydrocarbon group, an optionally substituted aryl group, an optionally substituted heterocyclic group or an optionally substituted condensed hetero cyclic group). There may be exemplified methylphosphoryl group, dimethylphosphoryl group and methylethylphosphoryl group. Carbon number(s) of such a substituent is/are preferably 1 to 20.

All of the above-mentioned compounds according to the present invention may be manufactured by known methods or methods similar thereto. Methods for the manufacture of the compounds of the present invention will be exemplified as follows.

In the case of the compound represented by the formula (5) where $R^1$ is not hydrogen, it can be manufactured by cyclization of a compound, for example, represented by the formula (11)

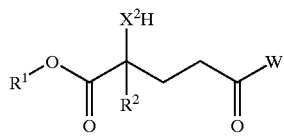

(in the formula, $R^1$, $R^2$ and $X^2$ are the same as those defined already; and W is a leaving group) by means of an intramolecular ring closing reaction.

Here, preferred leaving groups are the leaving groups which are known per se such as halogen, ester group, mercapto group, etc.

As to the condition for the intramolecular ring closure reaction, known conditions may be used. Thus, for example, heating is carried out in an organic solvent, preferably in toluene, at about 30 to 100° C. or, preferably, about 50 to 70° C. for about 5 to 20 hours or, preferably, about 8 to 15 hours.

After that, the solvent is usually removed. Removal of the solvent may be carried out under reduced pressure or in vacuo depending upon necessity.

If desired, purification may be carried out by known methods such as chromatography or filtration to give the compound represented by the formula (5).

In the case of the compound represented by the formula (5) where $R^1$ is hydrogen, a starting material where $R^1$ is a protective group such as benzyl group is firstly prepared and then it is hydrolyzed by a known method or by a method similar thereto.

Depending upon the type of the protective group represented by $R^1$, catalytic reduction may be carried out instead of hydrolysis. Condition for the catalytic reduction may follow the known reaction condition and there is exemplified a method where the starting material is brought into contact with hydrogen gas under ordinary or high pressure in the presence of a catalyst such as palladium-carbon, palladium hydroxide-carbon, platinum oxide or palladium black in an amount of about 3 to 20% by weight or, preferably, about 5 to 15% by weight.

If desired, purification may be carried out by known methods such as chromatography or filtration to give the compound represented by the formula (5).

In the case of the compound (6) where $R^1$ is not hydrogen and the substituent $X^2$ is O, the aimed compound is manufactured by adding a nucleophilic agent containing $X^1$ (definition of $X^1$ is the same as defined above) such as (COCl)$_2$ when X$^1$ is Cl or by adding a cyanide when X$^1$ is CN to a compound represented by the formula (12)

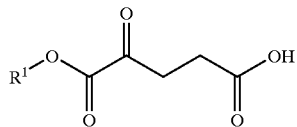

(in the formula, R$^1$ has the same meaning as defined already) in an organic solvent, preferably ether.

This reaction is believed to proceed in such a mechanism that an intramolecular ketalization firstly takes place and a nucleophilic agent attacks the resulting hydroxyl group.

After that, there is carried out an after-treatment such as removal of the solvent. Removal of the solvent may be carried out either under reduced pressure or in vacuo upon necessity.

If desired, purification may be carried out by known methods such as chromatography or filtration to give the compound represented by the formula (6).

In the case of the compound (7) where R$^1$ is not hydrogen, the substituent X$^2$ is O and R$^5$ and R$^6$ form a benzene ring together with the carbon atoms bonded thereto, a compound where X$^1$ is OH is synthesized by, for example, addition of 1,2-isochroman-1,3,4-trione to benzyl alcohol and pyridine.

After that, a nucleophilic agent containing X$^1$ (definition of X$^1$ is the same as defined above) to be manufactured such as (COCl)$_2$ is added when X$^1$ is Cl or, when X$^1$ is CN, a cyanide is added to substitute the OH group with the substituent X$^2$ to manufacture the aimed compound.

Such a reaction may be carried out according to conventional means.

The compounds represented by the above-mentioned formulae (1) to (7) may be metabolized in vivo, for example, as follows. Such metabolites may be a pharmaceutical according to the present invention as well.

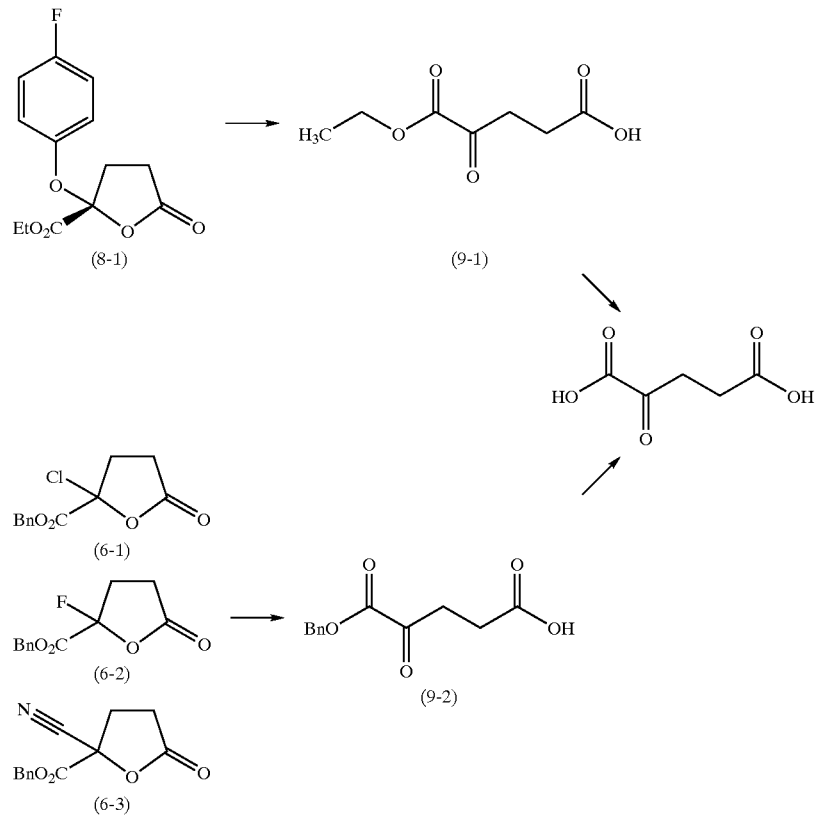

(in the formulae, Bn is benzyl group and Et is ethyl group)

The following compound (7-2), (7-3), (7-5) or (7-6) may be metabolized to a compound represented by the formula (7-1). In some cases, the following compound (7-2), (7-3) or (7-5) may also be metabolized to a compound where an ester group is converted to a carboxyl group.

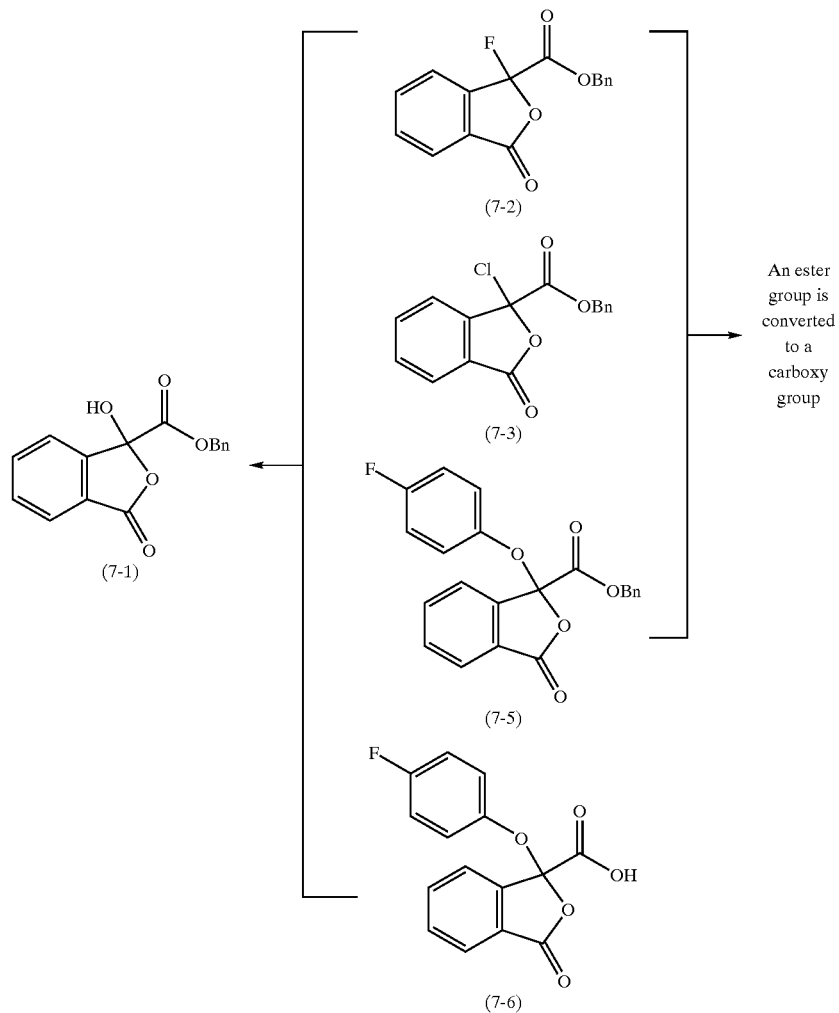

The pharmaceutical in accordance with the present invention may be in a dosage form such as tablets which are, if desired, sugar-coated or film-coated, capsules, elixirs or microcapsules and may be administered orally. Further, the pharmaceutical according to the present invention may be a parenteral preparation represented by injection such as an aseptic solution or suspension preparation with water or other pharmaceutically acceptable liquid.

The above-mentioned preparations may be manufactured by a method which is known per se.

The pharmaceutical according to the present invention may further contain other pharmacologically active component which is effective to progressive lesion after organic damage.

The pharmaceutical according to the present invention may still further contain additives which have been used in the related art such as binders, disintegrating agents, fillers, antiseptic agents, stabilizers and flavors.

With regard to the additive which may be mixed with tablets or capsules, there may be exemplified those which have been used in the related art such as binders, disintegrating agents, fillers, antiseptic agents, stabilizers and flavors. To be more specific, there may be used binders such as hydroxypropyl cellulose, hydroxypropyl methyl cellulose, Macrogol, gelatin, corn starch, tragacanth and gum arabic; disintegrating agents such as starch and carboxymethyl cellulose calcium; fillers such as lactose, starch and crystalline cellulose; swelling agents such as corn starch, gelatin and alginic acid; lubricants such as magnesium stearate and talc; sweeteners such as sucrose, lactose and saccharine; and flavors such as peppermint, oil derived from *Gaultheria ovatifolia* ssp. *Adenothrix* and cherry. When the dosage form is a capsule, it is also possible to add a liquid carrier such as fat/oil in addition to the above additives.

With regard to an aqueous solution for injection, it is possible to use a physiological saline and other isotonic solution containing glucose and other excipients such as D-sorbitol, D-mannitol and sodium chloride. In that case, it is further possible to jointly use the appropriate solubilization aids such as alcohol (e.g., ethanol), polyalcohol (e.g., propylene glycol and polyethylene glycol) and nonionic surface-active agent (e.g., Polysorbate 80™ and HCO-50). In the case of an oily liquid for injection, sesame oil, soybean oil, etc. may be used. Solubilizing aids such as benzyl benzoate and benzyl alcohol may be also used together therewith. It is also possible to compound with buffer such as phosphate buffer and sodium acetate buffer; anesthetizing agent such as benzalkonium chloride and procaine hydrochloride; stabilizer (such as human serum albumin and polyethylene glycol; preserving agent (antiseptic) such as chlorobutanol, methyl p-hydroxybenzoate, propyl p-hydroxybenzoate, benzyl alcohol and phenol; antioxidant; etc. The pharmaceutical preparation such as injection prepared as such is usually filled in appropriate ampoules.

Daily dose of the pharmaceutical of the present invention may vary depending upon the type of the effective ingredient, diseases to be treated, route for administration, dosage form, etc. and is not definitely decided. Preferably however, it is about 0.1 to 100 mg/kg, more preferably about 1 to 50 mg/kg and it is alsopossible to be about 0.5 to 50 mg/kg. Those compounds are of low toxicity and are able to be administered either orally or parenterally.

The compounds of the present invention represented by the above-mentioned formulae (1) to (7) have immunosuppressive or fibrosis inhibiting action. To be more specific, the compound according to the present invention exhibits an effect of selectively suppressing the effector macrophage expressed in the damaged tissue caused by organic damager or immune disease whereby it is able to selectively exhibit an immunosuppressive action selectively to specific tissues. Further, it is able to effectively inhibit the progress or worsening of the disease by the said effector macrophage whereby it specifically exhibits a fibrosis inhibiting action selectively to damaged tissues.

Accordingly, the pharmaceutical which contains the compound of the present invention represented by the above-mentioned formulae (1) to (7) is able to be used as an immunosuppressant or a fibrosis inhibitor. To be more specific, the pharmaceutical can be used for prevention of onset or progress of rejection upon allogeneic or xenogeneic cell, tissue or organ transplantation, acute or chronic glomerular nephritis, interstitial nephritis or diabetes mellitus; therapy and/or prevention of complications such as diabetic nephropathy, diabetic retinopathy and diabetic neuropathy; therapy and/or prevention of chronic pancreatitis, arteriosclerosis, arteriosclerotic restenosis, pulmonary fibrosis, dialytic amyloidosis, chronic hepatitis, cerebrospinal degenerative disease, asthma, rheumatic arthritis, chronic pigmentary dermatitis, psoriasis, autoimmune chronic organic tissue damage, endotoxin shock reaction by bacterial toxin, systemic intravascular coagulation and cancer or metastasis thereof; and prevention and therapy of aids virus infection. It may also be used as a substitute for steroidal therapeutic agents.

Daily dose of the above-mentioned pharmaceutical according to the present invention used as an immunosuppressants or a fibrosis inhibitor may vary depending upon the type of the effective ingredient, the disease to be treated, route of administration, dosage form, etc. and is not definitely decided. Preferably however, it is about 0.1 to 100 mg/kg, more preferably about 1 to 50 mg/kg and it is also possible to be about 0.5 to 50 mg/kg in terms of the compound represented by the formulae (1) to (7). Those compounds are of low toxicity and are able to be administered either orally or parenterally.

As mentioned above, the pharmaceutical according to the present invention which is used as an immunosuppressant or a fibrosis inhibitor may contain other pharmacological components showing an immunosuppressive action or a fibrosis inhibiting action as mentioned above. Further, it may be in various dosage forms as mentioned above and, still further, it may contain known additives depending upon the above-mentioned dosage form.

In the following Examples, Bn means a benzyl group.

EXAMPLE 1

Manufacture of (RS)-(−)-α-methyl-2-naphthalene-methyl 2-(4-fluorophenoxy)-5-oxotetrahydrofuran-2-carboxylate

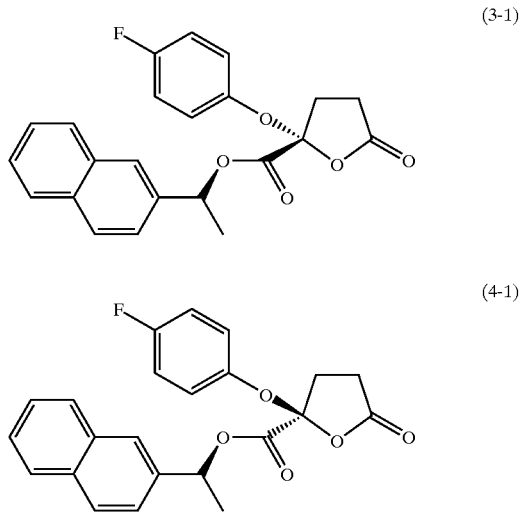

and

To a solution prepared by dissolving 164 mg (0.6 mmol, 1 equivalent) of 2-(4-fluorophenoxy)-5-oxotetrahydrofuran-2-carboxylic acid manufactured by a method mentioned in paragraph [0018], page 5 of Japanese Patent Laid-Open No. 04/338,331 in 2.2 ml of ether at 0° C. were added 240 μl (2.7 mmol, 4 equivalents) of (COCl)$_2$ gradually and then two drops of dimethylformamide (DMF) were added thereto. At that time, discharge of gas was observed.

The reaction solution was allowed to stand for 1 hour with stirring at 0° C., ether was removed in vacuo and the product was dried in vacuo.

The product was dissolved in 2.5 ml of ether, then 130 mg (0.75 mmol, 1.1 equivalents) of (S)-(−)-α-methyl-2-naphthalenemethanol and 8 mg (0.07 mmol, 0.1 equivalent) of dimethylaminopyrrolidone (hereinafter, abbreviated as DMAP) were gradually added and, at the same time, 140 μl (1 mmol, 1.5 equivalents) of triethylamine were added thereto as well.

After the reaction, the product is dissolved in 20 ml of ether, the solution was washed with an aqueous solution of NaHCO$_3$ and the organic phase was dried over MgSO$_4$.

The solvent was removed in vacuo and, as a result of the first purification by silica gel, 175 mg (yield: 74%) of the product were obtained. By means of purification using silica gel for several times thereafter, an optical isomer was separated from a mixture of two diastereomers.

About the compound of the formula (3), i.e. (S)-(−)-α-methyl-2-naphthalenemethyl 2-(4-fluorophenoxy)-5-oxotetrahydrofuran-2-carboxylate:

Thin-layer chromatography: R$_f$=0.56 (hexane/ether, 1:1 (v/v))

T$_f$=97–98° C.

[α]$^{23}_D$=−113 (c=3 in CHCl$_3$)

RMN $^1$H (300 MHz; CDCl$_3$) d ppm: 1.44 (3H, d, J=6.7 Hz); 2.47–2.8 (4H, m); 6.03 (1H, q, J=6.7 Hz); 6.82–6.88 (2H, m); 7.03–7.09 (2H, m); 7.34–7.35 (1H, m); 7.49–7.51 (2H, m); 7.73 (1H, s); 7.8–7.9 (3H, m).

RMN $^{13}$C (75 MHz; CDCl$_3$) dppm: 21.54; 27.4; 33.1; 75.5; 105.3; 116 (d, $^2J_{CF}$=23 Hz); 120.5 (d, $^3J_{CF}$=7.2 Hz);

123.8; 125.6; 126.6; 127.8; 128.2; 128.7; 133.1; 133.3; 137.2; 150.4; 159.3 (d, $^1J_{CF}$=244 Hz); 166.0; 174.0.

IR (CsI) v: 3423; 2981; 1797; 1758; 1504; 1290; 1194; 1165; 1082; 1044; 914; 857; 822; 751 cm$^{-1}$.

About the compound of the formula (4), i.e. (R)-(-)-α-methyl-2-naphthalenemethyl 2-(4-fluorophenoxy)-5-oxotetrahydrofuran-2-carboxylate:

Thin-layer chromatography: R$_f$=0.51 (hexane/ether, 1:1 (v/v))

T$_f$=117–118° C.

[α]$^{23}_D$=−20 (c=3 in CHCl$_3$)

RMN $^1$H (300 MHz; CDCl$_3$) d ppm: 1.62 (3H, d, J=6.7 Hz); 2.49–2.87 (4H, m); 6.05 (2H, q, J=6.7 Hz); 6.76–6.81 (2H, m); 6.82–7.1 (2H, m); 7.17 (1H, m); 7.5–7.6 (2H, m); 7.65 (1H, s); 7.7–7.8 (3H, m).

RMN $^{13}$C (75 MHz; CDCl$_3$) d ppm: 21.5; 27.41; 33.2; 75.6; 116 (d, $^2J_{CF}$=23 Hz); 120.4 (d, $^3J_{CF}$=8.6 Hz); 123.8; 125.8; 126.6; 127.7; 128.1; 128.6; 133.0; 136.9; 150.3; 159.5 (d, $^1J_{CF}$=255 Hz); 166.3; 174.0.

IR (CsI) v: 3423; 2981; 1797; 1758; 1504; 1290; 1194; 1165; 1082; 1044; 914; 857; 822; 751 cm$^{-1}$.

EXAMPLE 2

Manufacture of (±)-2-(4-fluorophenoxy)-5-oxotetrahydrofuran-2-carboxylic acid (a) Manufacture of (−)-2-(4-fluorophenoxy)-5-oxotetrahydrofuran-2-carboxylic acid

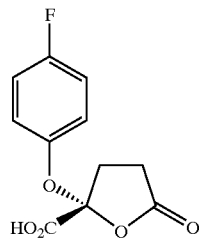

(2)

C$_{11}$H$_9$FO$_5$
Molecular weight=240.1
White solid
T$_f$=128° C.

To a solution of 98 mg (0.24 mmol, 1 equivalent) of (S)-(−)-α-methyl-2-naphthalenemethyl 2-(4-fluorophenoxy)-5-oxotetrahydrofuran-2-carboxylate represented by the formula (3-1) manufactured in Example 1 dissolved in 4 ml of ethyl acetate and 8 drops of ethanol was added a Pd/C catalyst in an amount of 10 parts by weight to 100 parts by weight of the above solution. The resulting solution was washed with water several times, stirred at room temperature and subjected to a catalytic reduction using hydrogen for 4 hours. The product was dissolved in ethyl acetate, the catalyst was removed by filtering through Celite (manufactured by Johns Manville Sales Co.) and the solvent was removed in vacuo. The product was purified by means of a reverse phase silica gel chromatography (RP 18) (eluent: acetonitrile/water, 1:1 (v/v)). Acetonitrile was removed in vacuo and an aqueous phase was freeze-dried. The present compound was white powder and 45 mg (yield: 78%) were prepared.

(b) (+)-2-(4-fluorophenoxy)-5-oxotetrahydrofuran-3-carboxylic acid

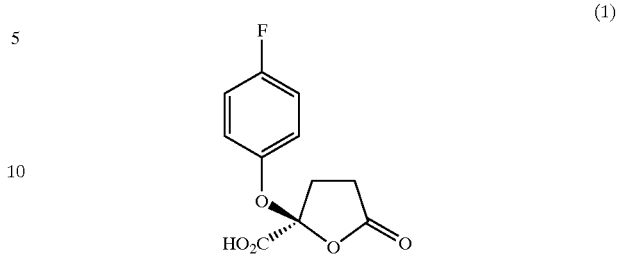

(1)

C$_{11}$H$_9$FO$_5$
Molecular weight=240.1
White solid
T$_f$=128° C.

(R)-(−)-α-methyl-2-naphthalenemethyl 2-(4-fluorophenoxy)-5-oxotetrahydrofuran-2-carboxylate represented by the formula (4-1) manufactured in Example 1 was subjected to a catalytic reduction with hydrogen in the same manner as above whereupon the present compound was selectively manufactured. The present compound was white powder and 16 mg (yield: 58%) were obtained.

Compound (1): [α]$^{23}_D$=−101 (c=0.6 in MeOH)
Compound (2): [α]$^{23}_D$=+116 (c=0.3 in MeOH)
RMN $^1$H (300 MHz; CDCl$_3$) d ppm: 2.63–2.84 (4H, m); 7.08–7.14 (4H, m).

RMN $^{13}$C (75 MHz; CDCl$_3$) d ppm: 26.7; 32.6; 105.7; 115.4 (d, $^2J_{CF}$=23 Hz); 120.5 (d, $^3J_{CF}$=8.6 Hz); 150.9; 159.2 (d, $^1J_{CF}$=235 Hz); 168.4; 175.1

IR (CsI) v: 3082; 1775; 1507; 1253; 1199; 1041; 978; 830; 708 cm$^{-1}$

EXAMPLE 3

Manufacture of benzyl 2-(4-fluorobenzyl)-5-oxotetrahydrofuran-2-carboxylate

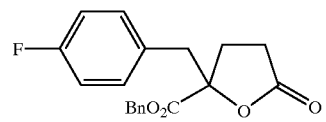

(5-1)

C$_{19}$H$_{17}$FO$_4$
Molecular weight=328.3
White crystals
T$_f$=70° C.

In the presence of Amberyst resin 15 (manufactured by Rohm & Haas Co.), a solution where 192 mg (0.4 mmol, 1 equivalent) of dibenzyl 2-(4-fluorobenzyl)-2-hydroxypentane-1,5-dicarboxylate were dissolved in 6 ml of anhydrous toluene was heated at 60° C. for 10 hours. This was returned to room temperature and filtered through cotton to remove the Amberyst resin 15. The solvent was removed in vacuo and the product was separated by chromatography (eluent: hexane/ethyl acetate, 8.5:2.5 (v/v)). After purification by recrystallization from ether-hexane twice, the present compound was obtained as thin flaky crystals in an amount of 99 mg (yield: 76%).

Thin-layer chromatography: R$_f$=0.24 (hexane/ethyl acetate, 7:3 (v/v))

RMN $^1$H (300 MHz; CDCl$_3$) d ppm: 2.15–2.52 (4H, m); 3.1 (1H, d, J=14.4 Hz); 3.3 (1H, d, J=14.4 Hz); 5.14 (1H, d, J=12 Hz); 5.18 (1H, d, J=12 Hz); 6.92 (2H, t, J=8.6 Hz); 7.1 (2H, t, J=8.6 Hz); 7.25–7.36 (5H, m).

RMN $^{13}$C (75 MHz; CDCl$_3$) d ppm: 27.8; 30.4; 41.6; 67.6; 86.1; 115.2 (d, $^2J_{CF}$=22 Hz); 128.3; 128.6; 129.5; 131.9 (d, $^3J_{CF}$=6.8 Hz); 134.7; 162.3 (d, $^1J_{CF}$=244 Hz); 170.8; 175.3.

IR (CsI) v: 1784; 1736; 1508; 1223; 1189; 1097; 1056; 973; 910; 840; 700; 607 cm$^{-1}$.

SM (IC/NH$_3$) m/z (intensite relative): 346=100% (MNH$_4^+$); 347=23%; 674=19% (2×M+NH$_4^+$).

EXAMPLE 4

Manufacture of 2-(4-fluorobenzyl)-5-oxo-tetrahydrofuran-2-carboxylic acid

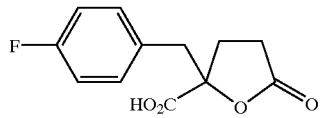

(5-2)

C$_{12}$H$_{11}$FO$_4$

Molecular weight=238.2

White crystals

T$_f$=93–94° C.

To a solution prepared by dissolving 71 mg (0.2 mmol, 1 equivalent) of benzyl 2-(4-fluorobenzyl)-5-oxo-tetrahydrofuran-2-carboxylate represented by the formula (5-1), manufactured by the above Example 3, in a mixture of 1.5 ml of ethyl acetate and 3 drops of ethanol was added a Pd/C catalyst in an amount of 10 parts by weight to 100 parts by weight of the above solution. The reaction solution was washed with water several times and subjected to a catalytic reduciton with hydrogen for 6 hours with stirring. Completion of the reaction was confirmed by means of a thin-layer chromatography.

The product was filtered through Celite (manufactured by Johns Manville Sales Co.) and the solvent was evaporated in vacuo. As a result, the present compound in white powder was obtained in an amount of 46 mg.

Thin-layer chromatography: R$_f$=0.23 (ethyl acetate/acetic acid, 98:2 (v/v))

RMN $^1$H (300 MHz; CDCl$_3$) d ppm: 2–2.55 (4H, m); 3.12 (H, d, J=14 Hz); 3.37 (1H, d, J=14 Hz); 7.01 (2H, t, J=8 Hz); 7.25 (2H, t, J=8 Hz); 8.01 (1H, s).

RMN $^{13}$C (75 MHz; CDCl$_3$) d ppm: 28.8; 31.9; 42.6; 88.0; 115.7 (d, $^2J_{CF}$=21 Hz); 132.2; 133.3 (d, $^3J_{CF}$=7.2 Hz); 163.5 (d, $^1J_{CF}$=242 Hz); 174.2; 178.3.

IR (CsI) v: 3124; 1769; 1511; 1409; 1270; 1244; 1223; 1178; 1037; 961; 933; 848; 773; 696; 658 cm$^{-1}$.

SM (IC/NH$_3$) m/z (relative intensity): 256=100% (MNH$_4^+$); 257=14%; 494=14% (2×M+NH$_4^+$).

EXAMPLE 5

Manufacture of benzyl 2-prop-2-ynyl-5-oxo-tetrahydrofuran-2-carboxylate

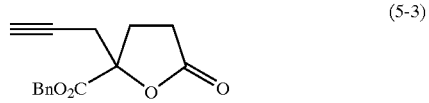

(5-3)

C$_{15}$H$_{14}$O$_4$

Molecular weight=258.2

Colorless liquid

In the presence of Amberyst resin 15 (manufactured by Rohm & Haas Co.), a solution of 160 mg (0.43 mmol, 1 equivalent) of dibenzyl 2-hydroxy-2-(2-prop-2-ynyl)pentane-1,5-dicarboxylate in 5 ml of anhydrous toluene was stirred overnight at 60° C.

When the reaction finished, the reaction solution was returned to ordinary temperature and spherical Amberyst resin was removed by filtering through cotton. The solvent was removed in vacuo.

The product was purified by a silica type chromatography (eluent: hexane/ethyl acetate, 7:3 (v/v)). The present compound was colorless liquid and was obtained in an amount of 85 mg (yield: 77%).

Thin-layer chromatography: R$_f$=0.23 (hexane/ethyl acetate, 7:3 (v/v))

RMN $^1$H (300 MHz; CDCl$_3$) d ppm: 2.08 (1H, t, J=2.6 Hz); 2.44–2.7 (4H, m); 2.89 (1H, dd, J=17.3 Hz, J=2.6 Hz); 2.95 (1H, dd, J=17.3 Hz, J=2.6 Hz); 5.22 (1H, d, J=12 Hz); 5.28 (1H, d, J=12 Hz); 7.38 (5H, ml).

RMN $^{13}$C (75 MHz; CDCl$_3$) d ppm: 27.1; 28.1; 29.5; 67.8; 72.2; 77.0; 83.9; 128.1; 128.6; 134.6; 169.8; 175.2. IR (CsI) v: 3286; 1793; 1746; 1456; 1419; 1339; 1261; 1170; 1068; 933; 753; 699 cm$^{-1}$.

SM (IC/NH$_3$) m/z (intensite relative): 276=100% (MNH$_4^+$); 277=19%; 534=16% (2×M+NH$_4^+$).

EXAMPLE 6

Manufacture of benzyl 2-benzyl-5-oxo-tetrahydrofuran-2-carboxylate

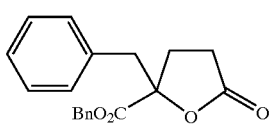

(5-4)

C$_{19}$H$_{18}$O$_4$

Molecular weight=310.3

White crystals

T$_f$=93–94° C.

In the presence of Amberyst resin 15 (manufactured by Rohm & Haas Co.), a solution of 180 mg (0.43 mmol, 1 equivalent) of dibenzyl 2-benzyl-2-hydroxypentane-1,5-dicarboxylate in 6 ml of anhydrous toluene was stirred overnight at 60° C.

When the reaction finished, the reaction solution was returned to ordinary temperature and spherical Amberyst resin was removed by filtering through cotton. The solvent was removed in vacuo.

The product was purified by a silica type chromatography (eluent: hexane/ethyl acetate, 8:2 (v/v)). The present compound was a white solid and was obtained in an amount of 84 mg (yield: 63%).

Thin-layer chromatography: $R_f$=0.27 (hexane/ethyl acetate, 7:3 (v/v))

RMN $^1$H (300 MHz; CDCl$_3$) d ppm: 2.1–2.5 (4H, m); 3.15 (1H, d, J=14.3 Hz); 3.38 (1H, d, J=14.3 Hz); 5.2 (2H, s), 7.2–7.38 (10H, m).

RMN $^{13}$C (75 MHz; CDCl$_3$) d ppm: 27.9; 30.1; 42.3; 67.7; 86.2; 127.4; 128.3; 128.5; 128.6; 128.7; 130.4; 171; 175.5.

IR (CsI) v: 1780; 1744; 1457; 1432; 1269; 1174; 1082; 1040; 914 857; 758; 701; 604 cm$^{-1}$.

SM (IC/NH$_3$) m/z (relative intensity): 328=100% (MNH$_4^+$); 329=34.

EXAMPLE 7

Manufacture of 2-benzyl-5-oxotetrahydrofuran-2-carboxylic acid

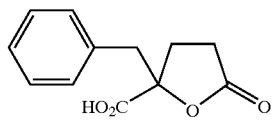

(5-5)

C12H12O4
Molecular weight=220.2
White crystals
$T_f$=110–111° C.

According to the manufacturing method for 2-(3-fluorobenzyl)-5-oxotetrahydrofuran-2-carboxylic acid (Example 4), the present compound in white solid was obtained in an amount of 34 mg (yield: 90%) from benzyl 2-benzyl-5-oxotetrahydrofuran-2-carboylate represented by the formula (5-4) manufactured in the above Example 6.

Thin-layer chromatography: $R_f$=0.19 (ethyl acetate/hexane/acetic acid, 6:4:0.2 (v/v/v)).

RMN $^1$H (300 MHz; CDCl$_3$) d ppm: 2.07–2.7 (6H, m); 3.16 (1H, d, J=14.3 Hz); 3.39 (1H, d, J=14.3 Hz); 7.19–7.35 (5H, m); 7.88 (1H, sl).

RMN $^{13}$C (75 MHz; CDCl$_3$) d ppm: 27.9; 29.9; 42.2; 86.0; 127.5; 128.5; 130.5; 133.5; 175.5; 176.1.

IR (CsI) v: 3032; 2938; 1782; 1712; 1185; 1082; 1044; 930; 746; 698 cm$^{-1}$.

SM (IC/NH$_3$) m/z (relative intensity): 238=100% (MNH$_4^+$); 239=15.

EXAMPLE 8

Manufacture of benzyl 2-chloro-5-oxotetrahydrofuran-2-carboxylate

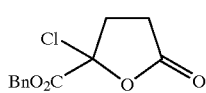

(6-1)

C$_{12}$H$_{11}$ClO$_4$
Molecular weight=254.6
Yellow oil

To a solution of 7.5 g (31.7 mmol, 1 equivalent) of benzyl 2-oxohemiglutarate dissolved in 105 ml of ether at 0° C. were added 8.3 ml (98 mmol, 3 equivalents) of (COCl)$_2$ and then DMF (400 μl) was added as well. At that time, discharge of gas was observed.

The mixture was stirred at 0° C. for 1 hour and then stirred at ordinary temperature for 2 hours. The temperature was set at 0° C. and the product was gradually neutralized with an aqueous solution of K$_2$CO$_3$. The product was extracted from ether (2×150 ml). The extracted organic phase was washed with water. After that, the reaction solution was dried over MgSO$_4$ and the solvent was removed in vacuo. The residue was added to a column filled with silica gel and purified by passing an eluent of hexane/ethyl (7:3 (v/v)) through the column to give 8 g of the present invention product as yellowish oil.

Thin-layer chromatography: $R_f$=0.4 (hexane/ethyl acetate, 7:3 (v/v))

RMN $^1$H (200 MHz; CDCl$_3$) d ppm: 2.48–2.89 (4H, m); 5.23 (2H, s); 7.25–7.35 (5H, m).

RMN $^{13}$C (50 MHz; CDCl$_3$) d ppm: 26.6; 35.9; 68.6; 96.4; 128.1; 128.6; 134.1; 164.6; 172.5.

IR (CsI) v: 1817; 1762; 1271; 1166; 1088 cm$^{-1}$.

SM (IC/NH$_3$) m/z (relative intensity): 255=13% (MH$^+$); 272=100% (MNH$_4^+$); 273=15%.

EXAMPLE 9

Manufacture of benzyl 2-fluoro-5-oxotetrahydrofuran-2-carboxylate

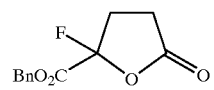

(6-2)

C$_{12}$H$_{11}$FO$_4$
Molecular weight=238.2
White crystals
$T_f$=57–58° C.

To a solution of 1 g (4.23 mmol, 1 equivalent) of benzyl 2-oxohemiglutarate dissolved in 10 ml of methylene chloride was added a solution of 670 μl (5 mmol, 1.2 equivalents) of diethylaminotrifluorosulfonic acid (hereinafter abbrivated as DAST) in 4 ml of methylene chloride at 0° C. After mixing, the reaction solution becomes dark red and was placed in a darkroom of 4° C. for 48 hours. The product was adsorbed on silica gel and separated by a silica type chromatography (eluent: hexane/ethyl acetate, 8.5:1.5 (v/v)). The present compound was white crystalline and obtained in an amount of 725 mg (yield: 72%).

Thin-layer chromatography: $R_f$=0.3 (hexane/ethyl acetate, 8:2 (v/v)).

RMN $^1$H (300 MHz; CDCl$_3$) d ppm: 2.48–2.91 (4H, m); 5.3 (1H, d, J=12 Hz); 5.39 (1H, d, J=12 Hz); 7.44 (5H, sl).

RMN $^{13}$C (75 MHz; CDCl$_3$) d ppm: 26.1; 30.6 (d, $^2J_{CF}$=26 Hz); 68.8; 11.2 (d, $^1J_{CF}$=238 Hz); 128.6; 128.9; 129.0; 134.2; 164.3 (d, $^2J_{CF}$=36 Hz); 173.0.

IR (CsI) v: 1815; 1764; 1339; 1313; 1199; 1177; 1103; 1058; 973; 908; 776; 751; 699 cm$^{-1}$.

SM (IC/NH$_3$) m/z (relative intensity): 256=100% (MNH$_4^+$); 257=12%.

Incidentally, the compound represented by the formula (6-5)

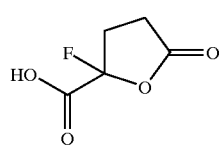

(6-5)

was able to be manufactured according to the method of Example 4 from benzyl 2-fluoro-5-oxotetrahydrofuran-2-carboxylate manufactured in this Example.

EXAMPLE 10

Manufacture of benzyl 2-cyano-5-oxotetrahydrofuran-2-carboxylate

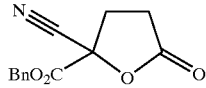

(6-3)

$C_{12}H_{11}FO_4$

Molecular weight=238.2

White crystals $T_f$=57–58° C.

To a solution where 200 mg (0.78 mmol, 1 equivalent) of benzyl 2-chloro-5-oxotetrahydrofuran-2-carboxylate manufactured in Example 8 was dissolved in 1.2 ml of tetrahydrofuran (THF) was added at −78° C. a solution of 209 mg (0.78 mmol, 1 equivalent) of cyanotetrabutylammonium dissolved in 1.5 ml of THF. The reaction solution soon became red. This was stirred at −78° C. for 15 minutes. The reaction solution was returned to ordinary temperature and gradually mixed with a mixture of 5 ml of ether and 5 ml of water. After that, water was removed by ether (2×15 ml) and an organic phase was collected. The organic layer was washed with water and dried over $Na_2SO_4$. After removal of the solvent, the residue was added to a column filled with silica gel and purified by adding an eluent hexane/ethyl acetate (7:3 (v/v)). The brown oil obtained at that time was further purified. The present compound was a white solid and obtained in an amount of 177 mg (yield: 93%)

Thin-layer chromatography: $R_f$=0.3 (hexane/ethyl acetate, 7:3 (v//v))

RMN $^1$H (300 MHz; $CDCl_3$) dppm: 2.64–2.85 (4H, m); 5.35 (2H, s); 7.4 (5H, ml).

RMN $^{13}$C (75 MHz; $CDCl_3$) dppm: 25.9; 32; 69.6; 74.6; 114.6; 128.3; 128.7; 129.0; 133.4; 163.8; 172.4.

IR (CsI) v: 3035; 1815; 1764; 1498; 1456; 1417; 1379; 1271; 1158; 1072; 1048; 961; 895; 754; 698 cm$^{-1}$.

SM (IC/$NH_3$) m/z (relative intensity): 263=100% ($MNH_4^+$); 264=12%; 280=24%.

EXAMPLE 12

Manufacture of benzyl 1-hydroxy-3-oxo-1,3-dihydroisobenzofuran-1-carboxylate

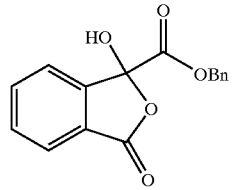

(7-1)

$C_{16}H_{12}O_5$

Molecular weight=284.2

White solid $T_f$=77° C.

To a solution of 500 mg (2.84 mmol, 1 equivalent) of 1,2-isochroman-1,3,4-trione dissolved in 6.5 ml of THF were added 292 μl (2.84 mmol, 1 equivalent) of benzyl alcohol and 230 μl (2.84 mmol, 1 equivalent) of pyridine. The reaction solution which was yellow at first became transparent after 15 minutes. The reaction solution was stirred at ordinary temperature for 2 hours.

After that, the solvent was removed in vacuo. The product was dissolved again in a mixture of chloroform and water and, after that, an aqueous phase was extracted with chloroform (3×20 ml). The organic phase was washed with 5% by volume of hydrochloric acid and with water. The organic phase was dried over $Na_2SO_4$ and the solvent was removed in vacuo. The product was purified by chromatography using silica gel (eluent: hexane/ethyl acetate, 6:4 (v/v)). The present compound was a white solid and obtained in an amount of 605 mg (yield: 75%).

Thin-layer chromatography: $R_f$=0.23 (hexane/ethyl acetate, 6:4 (v/v)

RMN $^1$H (300 MHz; $CDCl_3$) d ppm: 5.24 (2H, s); 7.15–7.33 (1H, d, J=7.5 Hz); 7.64–7.76 (2H, m); 7.9 (1H, d, J=6.7 Hz).

RMN $^{13}$C (75 MHz; $CDCl_3$) d ppm: 68.9; 122.8; 125.7; 126.8; 127.7; 128.5; 128.6; 131.3; 133.9; 134.7; 144.6; 167.4; 167.8.

IR (CsI) v: 3384; 1746; 1467; 1277; 1237; 1202; 1157; 1105; 1083; 907; 750; 694 cm$^{-1}$.

SM (IC/$NH_3$) m/z (relative intensity): 302=100% ($MNH_4^+$); 303=22%.

EXAMPLE 13

Manufacture of benzyl 1-fluoro-3-oxo-1,3-dihydro-isobenzofuran-1-carboxylate

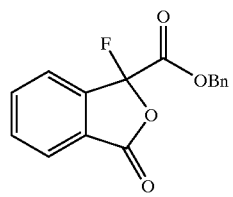

(7-2)

$C_6H_{11}O_4$

Molecular weight=302.7

White solid $T_f$=78° C.

To a solution where 300 mg (1.05 mmol, 1 equivalent) of benzyl 1-hydroxy-3-oxo-1,3-dihydroisobenzofuran-1-carboxylate represented by the formula (7-1) manufactured in the above Example 12 were dissolved in 2 ml of methylene chloride was added at 0° C. a solution of 167 μl (1.22 mmole, 1 equivalent) of DAST dissolved in 1.5 ml of methylene chloride. After addition, the reaction solution was stirred at 4° C. for 20 hours. The product was dissolved in methylene chloride, directly adsorbed on silica gel and then purified by silica gel chromatography (eluent: hexane/ethyl acetate, 8:2 (v/v)). The present compound was colorless oil and obtained in an amount of 213 mg (yield: 71%).

Thin-layer chromatography: $R_f$=0.3 (hexane/ethyl acetate, 8:2 (v/v))

RMN $^1$H (300 MHz; CDCl$_3$) d ppm: 5.2 (1H, d, J=12 Hz); 5.3 (1H, d, J=12 Hz); 7.29–7.38 (5H, m); 7.68–7.81 (3H, m); 7.95–7.98 (1H, dd, J=6.7 Hz, J=1.8 Hz).

RMN $^{13}$C (75 MHz; CDCl$_3$) d ppm: 68.7; 107.2 (d, $^1J_{CF}$=238 Hz); 123.4; 126.1; 132.6; 135.4; 125.4; 128.2; 128.6; 128.8; 142 (d, $^2J_{CF}$=20 Hz); 163.3 (d, $^2J_{CF}$=38.9 Hz); 165.7.

IR (CsI) ν: 3035; 1811; 1766; 1605; 1498; 1468; 1456; 1380; 1341; 1296; 1256; 1200; 1163; 1129; 1107; 1083; 1046; 965; 905; 749; 688; 594 cm$^{-1}$.

SM (IC/NH$_3$) m/z (relative intensity): 320=100% (MNH$_4^+$); 305=25%.

EXAMPLE 14

Manufacture of benzyl 1-chloro-3-oxo-1,3-dihydro-isobenzofuran-1-carboxylate

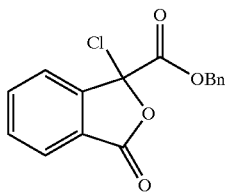

(7-3)

C$_{16}$H$_{11}$O$_4$Cl

Molecular weight=302.7

White solid

T$_f$=78° C.

Into 0.5 ml of ether were dissolved 50 mg (0.17 mmol, 1 equivalent) of benzyl 1-hydrodxy-3-oxo-1,3-dihydro-isobenzofuran-1-carboxylate represented by the formula (7-1) manufactured in the above Example 12. The solution was cooled at 0° C. and 80 μl (0.8 mmol, 5 equivalents) of (COCl)$_2$ and 3 drops of DMF were added thereto. At that time, discharge of gas and precipitate of white turbidity were observed. The reaction solution was returned to ordinary temperature and stirred for 3 hours. After the reaction, the product was dissolved in an aqueous solution of K$_2$CO$_3$, and the aqueous phase was extracted with ether (3×10 ml). The organic phase was washed with water and the solution was dried over Na$_2$SO$_4$. The solvent was removed in vacuo. There is no need to purify the present compound whereupon 51 mg of white solid were obtained.

Thin-layer chromatography: $R_f$=0.4 (hexane/ethyl acetate, 8:2 (v/v)).

RMN $^1$H (300 MHz; CDCl$_3$) d ppm: 5.32 (2H, s); 7.35–7.38 (5H, m); 7.66–7.95 (4H, m).

RMN $^{13}$C (75 MHz; CDCl$_3$) d ppm: 69.2; 91.9; 124; 124.3; 125.8; 131.8; 135.5; 128.2; 128.7; 128.8; 134; 146.3; 163.8; 166.

IR (CsI) ν: 3034; 1804; 1764; 1603; 1468; 1456; 1288; 1237; 1188; 1114; 1042; 985; 960; 905; 746; 697 cm$^{-1}$.

SM (IC/NH$_3$) m/z (relative intensity): 286=100%; 320=95% (MNH$_4^+$); 321=22%.

EXAMPLE 15

Manufacture of benzyl 3-oxo-1,3-dihydroisobenzofuran-1-carboxylate

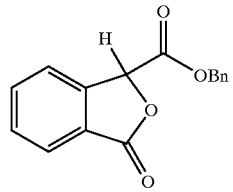

(7-4)

C$_{16}$H$_{12}$O$_4$

Molecular weight=268.2

White solid

T$_f$=101° C.

To a solution where 133 mg (0.43 mmol, 1 equivalent) of benzyl 1-chloro-3-oxo-1,3-dihydroisobenzofuran-1-carboxylate represented by the formula (7-3) manufactured in the above Example 14 were dissolved in 6 ml of benzene were gradually added 122 μl (0.46 mmol, 1.05 equivalents) of Bu$_3$SnH and 4 mg (0.02 mmol, 0.05 equivalent) of α,α'-azoisobutyronitrile (AIBN). The reaction solution was stirred at 70° C. for 5 hours and then stirred overnight at ordinary temperature. After the reaction, the solvent was removed in vacuo. The product was placed in ether and washed with a 10% by volume of KF solution. The organic phase was dried over Na$_2$SO$_4$ and the solvent was removed in vacuo. The residue was purified by a silica gel chromatography (eluent: hexane/ether, 7:3 (v/v)). The present compound was a white solid and obtained in an amount of 26 mg (yield: 23%).

Thin-layer chromatography: $R_f$=0.32 (hexane/ether, 6:4 (v/v))

RMN $^1$H (300 MHz; CDCl$_3$) d ppm: 5.17 (1H, d, J=12 Hz); 5.23 (1H, d, J=12 Hz); 5.86 (1H, s); 7.3 (5H, m); 7.65–7.51 (3H, m); 7.83 (1H, d, J=7 Hz).

RMN $^{13}$C (75 MHz; CDCl$_3$) d ppm: 68.0; 77.2; 122.7; 126.0; 130.2; 125.0; 128.4; 128.7; 128.8; 134.5; 143.9; 166.5; 169.3.

IR (CsI) ν: 3493; 3069; 2966; 1780; 1758; 1601; 1468; 1455; 1378; 1320; 1281; 1256; 1215; 1197; 1058; 1040; 949; 895; 755; 734; 697 cm$^{-1}$.

SM (IC/NH$_3$) m/z (relative intensity): 286=100% (MNH$_4^+$); 287=227%, 554=17% (2×M+NH$_4^+$).

EXAMPLE 16

Manufacture of benzyl 1-(4-fluorophenoxy)-3-oxo-1,3-dihydroisobenzofuran-1-carboxylate

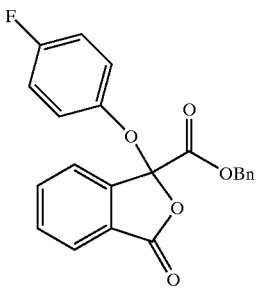

(7-5)

$C_{22}H_{15}O_5$

Molecular weight=378.34

White solid $T_f$=75° C.

A solution where 450 mg (1.5 mmol, 1 equivalent) of benzyl 1-hydroxy-3-oxo-1,3-dihydrobenzofuran-1-carboxylate represented by the formula (7-1) manufactured in the above Example 12 and 532 mg (4.75 mmol, 3 equivalents) of 4-fluorophenol were dissolved in 2 ml of methylene chloride was heated at 65° C. for 5 minutes. After heating, it was gradually added drop-by-drop to a solution where 355 mg (1.7 mmol, 1 equivalent) of N,N-dicyclohexylcarbodiimide (DCC) were dissolved in 0.8 ml of methylene chloride. After addition, the reaction solution was heated to reflux for 2.5 hours and the reaction container was returned to ordinary temperature followed by diluting with 10 ml of methylene chloride. The precipitate was removed by filtration and the solvent was removed in vacuo. The product was purified by chromatography using silica gel ($CH_2Cl_2$/hexane, 6:4 (v/v)). The present compound was a white solid and obtained in an amount of 227 mg (yield; 40%).

Thin-layer chromatography: $R_f$=0.27 ($CH_2Cl_2$/hexane, 6:4 (v/v)).

RMN $^1$H (300 MHz; $CDCl_3$) d ppm: 5.1 (1H, d, J=12 Hz); 5.2 (1H, d, J=12 Hz); 6.85–7.17 (4H, m); 7.28–7.34 (5H, m); 7.64–7.92 (4H, m).

RMN $^{13}$C (75 MHz; $CDCl_3$) d ppm: 68.5; 103.2; 115.9 (d, $^2J_{CF}$=23 Hz); 121.5 (d, $^3J_{CF}$=8 Hz); 123.9; 125.8; 128.6; 131.9; 126.2; 128.2; 128.5; 134; 134.9; 143.6; 149.4; 159.4 (d, $^1J_{CF}$=242 Hz); 164.9; 166.9.

IR (CsI) v: 1790; 1747; 1603; 1506; 1465; 1272; 1258; 1205; 1097; 1040; 996; 959; 830; 784; 741; 697 cm$^{-1}$.

SM (IC/NH$_3$) m/z (relative intensity): 396=100% (MNH$_4^+$); 397=33%.

EXAMPLE 17

Manufacture of 1-(4-fluorophenoxy)-3-oxo-1,3-dihydro-isobenzofuran-1-carboxylic acid

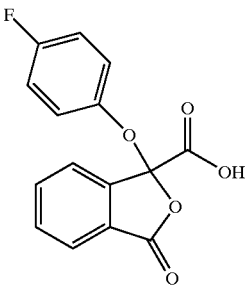

(7-6)

$C_{15}H_9O_5$

Molecular weight=288.2

White solid $T_f$=143–147° C.

To a solution where 40 mg (0.1 mmol, 1 equivalent) of benzyl 1-(4-fluorophenoxy)-3-oxo-1,3-dihydroisobenzofuran-1-carboxylate represented by the formula (7-5) manufactured in the above Example 16 were dissolved in a mixture of 1.2 ml of ethyl acetate and 2 drops of ethanol was added a Pd/C catalyst in an amount of 10 parts by weight to 100 parts by weight of the said solution. After the reaction solution was degassed several times, it was subjected to a catalytic reduction with hydrogen with stirring at ordinary temperature for 1 hour. The catalyst was removed by filtering through Celite (manufactured by Johns Manville Sales Co.). The solvent was removed in vacuo. The compound was a white solid and obtained in an amount of 28 mg.

Thin-layer chromatography: $R_f$=0.16 (ethyl acetate/methanol/acetic acid, 95:0.5:0.1 (v/v/v)).

RMN $^1$H (300 MHz; $CDCl_3$) d ppm: 6.97–7.19 (4H, m); 7.70–7.88 (4H, m).

RMN $^{13}$C (75 MHz; $CDCl_3$) d ppm: 105; 116.7(d, $^2J_{CF}$=23 Hz); 123.3 (d, $^3J_{CF}$=8.6 Hz); 125.3; 126.4; 133.1; 136.3; 127.5; 145.5; 151.2; 160.9 (d, $^1J_{CF}$=239 Hz); 168.0; 168.2.

IR (CsI) v: 3448; 1797; 1734; 1501; 1466; 1257; 1188; 1099; 1032; 960; 851; 783; 727 cm$^{-1}$.

SM (IC/NH$_3$) m/z (relative intensity): 306=100% (MNH$_4^+$); 307=24% 594=23% (2×M+18).

EXAMPLE 18

Manufacture of the compound of the following formula

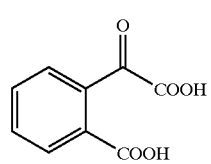

(7-8)

$C_9H_6O_5$

Molecular weight=194.1

White solid $T_f$=130–140° C.

Isochroman-1,3,4-trione (64 mg, 0.36 mmol, 1 equivalent) was dissolved in 0.5 ml of water followed by stirring overnight at ordinary temperature. After that, the reaction solution was frozen and then freeze-dried. No purification was necessary and the present compound was obtained white solid in an amount of 69 mg.

RMN ¹H (300 MHz; CDCl₃) d ppm: 7.61–7.91 (4H, m).

RMN ¹³C (75 MHz; CDCl₃) d ppm: 123.1 (sl); 125.1 (sl); 131.8; 134.6 (sl); 168.8 (sl).

IR (CsI) v: 3494; 3067; 1777; 1745; 1467; 1386; 1285; 1232; 1197; 1163; 1104; 1079; 1001; 930; 769; 706 cm⁻¹.

n SM (IC/NH₃) m/z (relative intensity): 212=100% (MNH₄⁺); 229=85%.

EXAMPLE 19

Manufacture of (RS)-(+)-α-methyl-2-naphthalene-methyl 2-(4-fluorophenoxy)-5-oxotetrahydrofuran-2-carboxylate

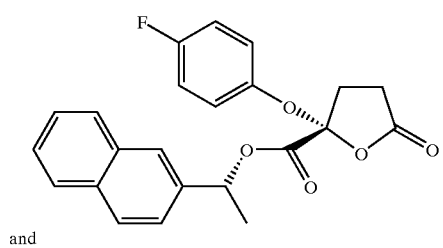
(3-2)

and

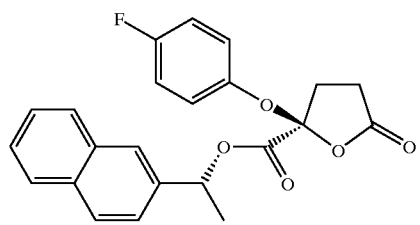
(4-2)

The above two compounds were manufactured by the same manner as in Example 1.

The above γ-lactone derivatives may be classified into the following groups A–D when the conventional gamma-lactone immunosuppressive compound (a racemate of ethyl 2-(4-fluorophenoxy)-5-oxo-2-tetrahydrofurancarboxylate mentioned in Japanese Patent Laid-Open No. 04/338,331) is taken as a lead compound.

Group A: compounds where the conventional compound which is racemic is separated into single compounds which are optical isomers Group B: compounds where oxocyclic oxygen of the lead compound is substituted with carbon which are more stable to an enzymatic hydrolysis and show an activity similar to the lead compound.

Group C: compounds where 4-fluorophenoxy group of the lead compound is substituted with an unstable substituent such as halogen, alkoxy group, benzoxy group, nitrile group, etc. Incidentally, such compounds may also be grasped as prodrugs of ketoglutaric acid having activity.

Group D: compounds where an aromatic ring is added to the lead compound for stability of the compound and, in addition, 4-fluorophenoxy group or halogen is introduced for affinity to lipid. Such compounds may also be grasped as a compound represented by the formula (7-1) having activity and prodrugs thereof.

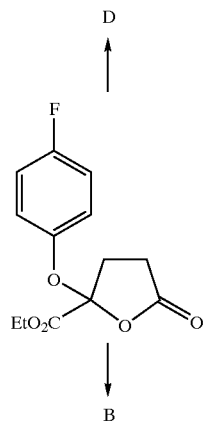

compounds represented by (7), preferably (7-1), (7-2), (7-3), (7-4), (7-5) and (7-6)

D coupounds represented by (6), preferably (6-1), (6-2), (6-3) and (6-4)    C compounds represented by (1), (2) or (3), preferably (3-1) and (3-2); compounds represented by (4), preferably (4-1) and (4-2)    A

B compounds represented by (5), preferably (5-1), (5-2), (5-3), (5-4) and (5-5))

(1) Evaluation of effector macrophage suppressive action showing a selective suppressive action to target cell damage in vitro A suppressive effect of the test compound to effector macrophage induction was investigated in vitro by an induction and production system of spontaneous plaque-forming cell (SPEC) mentioned in M. Ishibashi, S. Jiang, Y. Kokado, S. Takahara, T. Sonoda: Immunopharmacologic effects of immunosuppressive agents explored by a new effector generation assay. *Transplant Proc.*, 21:1854–1858, 1989.

TEST EXAMPLE 1

(Step 1: Separation of Human PBMC)

Heparin-added peripheral blood (40 ml) was collected from a healthy person and the same amount of EDTA-added physiological saline was added. PBMC were obtained by a specific gravity centrifugal method using Ficoll-Hypaque (manufactured by Pharmacia Fine Chemicals). Self-plasma was added thereto and allowed to stand at 37° C. for 10 minutes and platelets were removed by a low-speed centrifugal separation. RPMI 1640 liquid containing 15 µg/ml of gentamicin and 2 mM L-glutamine was used for washing the PBMC. Concentration of the PBMC was adjusted to $2 \times 10^6$ cells/ml using the same liquid.

(Step 2: Addition of an Agonist and a Substance to be Tested)

Each 200 µl of a solution containing $2 \times 10^6$ PBMC/ml prepared in the step 1 were added to each well of a micro test plate, lipopolysaccharide (hereinafter, abbreviated as LPS) was diluted with the RPMI 1640 liquid to make the final concentration 80 µg/ml and the said LPS solution was added to each well of the 200 µl-micro test plate. Further, each 50 µl of human serum of type AB were added so as to make the concentration 10% by weight. Two such micro test plates were prepared.

After that, to the above two micro test plates was added a solution where the test compound was diluted with 1% by weight of DMSO so as to make the concentration of the test compound 1 µM. Similarly were prepared each two micro test plates where the final concentrations of the test compound were 0.1 µM, 0.01 µM and 0.001 µM.

The culture liquid prepared as such was incubated for 6 days at 37° C. in 5% $CO_2$.

(Step 3: Recovery of the Incubated PBMC)

The effector macrophage induced after the incubation was all recovered using a rubber-policeman (spatula made of rubber). A Hanks solution containing 5 µg/ml of gentamicin was used for washing and, using the said solution, there was prepared a solution where the concentration of the induced effector macrophage was $2 \times 10^6$ per ml.

(Step 4: Preparation of Monolayered Autologous Erythrocyte-adhered Plate)

With regard to autologous erythrocytes, those which were preserved at 4° C. in a phosphate physiological saline (hereinafter, abbreviated as PBS) to which 0.1% by weight of AB serum and autologous erythrocytes obtained from PBMC separation were used were used. The preserved autologous erythrocytes were washed for three times with a Hanks solution to which no serum was added and made into a solution of 4% by weight concentration using the said Hanks solution. Poly-L-lysine was added to a Terasaki plate and washed with PBS every 20 minutes at 37° C., the above-mentioned autologous erythrocyte solution was added thereto immediately, the mixture was allowed to stand at 37° C. for 30 minutes and the erythrocytes which were not adhered to the plate were removed to prepare a Terasaki plate to which self-erythrocytes in a monolayer were adhered.

A Hanks solution (4 µl) was added to the said Terasaki plate, 4 µl of a solution containing the induced effect or macrophage obtained in the step 3 were added thereto and the mixture was allowed to stand at 37° C. for 2 hours. After completion of the reaction, it was fixed by formalin. Numbers of the produced SPFC which were adhered or phagocytized were measured.

(Step 5: Calculation of Total Amount of SPFC Produced)

A mean SPFC production number was calculated from the measured values of SPFC production when the concentration of the test compound was the same. SPFC production number per $1 \times 10^6$ of the induced effector macrophage was calculated and, from the recovered induced effector macrophage numbers, total SPFC production amount (S2) was calculated.

(Step 6: Judgment of Positive Compound Having the Activity)

As a control, no test compound was added and the same operation as above was carried out to calculate the total SPFC production amount (S1). The concentration of the test compound in which the total SPFC production amount when test compound was added (S2) was one half of that when no test compound was added (S1) was defined as $IC_{50}$. The test compound when its $IC_{50}$ was 1 µM or less was judged to be positive.

TEST EXAMPLE 2

The same operation as in Test Example 1 was carried out except that, in the step 2, mitomycin-treated human PBMC (allogenic MLC; hereinafter, abbreviated as allo-MLC) was added to each well of the micro test plate so as to make its concentration $2 \times 10^6$ per ml.

Here, the allo-MLC used was prepared in such a manner that mitomycin was added to PBMC which was prepared by the same manner as in the step 1 of Test Example 1 so as to make the concentration of mitomycin 40 µg/ml followed by allowing to stand at 37° C. for 30 minutes.

The result is shown in the following Table. The term "structure characteristic" in the Table means the above-mentioned groups A–D. With regard to a functional classification of the compound, the compound which selectively suppresses the SPFC production under the conditions of allo-MLC stimulation or, in other words, the compound which selectively suppresses the induction of effector macrophage in the presence of allo-MLC is classified as group I while the compound which selectively suppresses the SPFC production under the conditions of LPS stimulation or, in other words, the compound which selectively suppresses the induction of effector macrophage in the presence of LPS is classified as group II. Further, the compound which selectively suppresses the SPFC production under the conditions of both allo-MLC stimulation and LPS stimulation or, in other words, the compound which non-selectively suppresses the induction of effector macrophage is classified as group III. Each of the "compound" in the Table is the compound bearing the above-mentioned number.

TABLE 1

| Structure Characteristic | Compound | SPFC Production Inhibiting Concentration by all-MLC Stimulation ($\mu$M: $IC_{50}$) | SPFC Production Inhibiting Concentration by LPS Stimulation ($\mu$M: $IC_{50}$) | Functional Classification |
|---|---|---|---|---|
| A | (1) | 0.01 | >1.0 | Group I |
|   | (2) | >1.0 | 1 | Group II |
|   | (3-2) | >1.0 | 1 | Group II |
|   | (4-2) | 0.01 | >1.0 | Group I |
| B | (5-2) | 0.1 | 0.01 | Group II |
|   | (5-4) | 0.01 | 1 | Group I |
| C | (6-1) | >1.0 | 0.001 | Group II |
|   | (6-2) | not done | 0.001 | Group II |
|   | (6-3) | 0.1 | 0.001 | Group II |
| D | (7-1) | 0.1 | 1 | Group I |
|   | (7-2) | >1.0 | 0.1 | Group II |
|   | (7-3) | 0.01 | >1.0 | Group I |
|   | (7-5) | 0.01 | >1.0 | Group I |
|   | (7-6) | >1.0 | 0.01 | Group II |
|   | (7-7) | >1.0 | 0.01 | Group II |
| Metabolite | (9-1) | 0.01 | >1.0 | Group I |
| Conventional Compound |  | 0.1 | 0.1 | Group III |

In the Table, "Conventional Compound" is a racemic ethyl 2-(4-fluorophenoxy)-5-oxo-2-tetrahydrofurancarboxylate.

The optical isomer according to the present invention selectively suppressed the SPFC production by allo-MLC stimulation and that by LPS stimulation. The correlation in the biological activity depending upon the structure as such was confirmed in the two types of optical isomers of "(1) and (2)" and "(3-2) and (4-2)".

With regard to the compounds (group I) where SPFC production by allo-MLC stimulation is selectively suppressed, i.e., induction of effector macrophage in the presence of allo-MLC is selectively suppressed, the compounds represented by the formulae (1), (4-2), (5-4), (7-1), (7-3) and (7-5) correspondeded thereto. With regard to the compounds (group II) where SPFC production by LPS stimulation is selectively suppressed, i.e., induction of effector macrophage in the presence of LPS is selectively suppressed, the compounds represented by the formulae (2), (3-2), (5-2), (6-1), (6-2), (6-3), (7-2), (7-6) and (7-7) corresponded thereto. There were some compounds where the SPFC production suppressive activity was from 10-fold to 100-fold as compared with the conventional compound.

(2) Evaluation of immunosuppressive action showing a selective suppressive effect on target cell damage in animal experiments

TEST EXAMPLE 3

Obstruction release model after complete obstruction of unilateral ureter for 14 days Experimental models were prepared by a method devised and established by Ishibashi (Michio Ishibashi, et al.: *The Japanese Journal of Nephrology*, 42:248, 2000) using male SD rats of 8–9 weeks age and about 280 g. Thus, the rat was laparotomized under anesthetization with ether and ureter was ligated with 7-0 Nylon at the height of the margin of lower pole of left kidney to close the abdomen. On the 14th day after obstruction, the obstruction was released and urinary passage was reconstructed using a cuff. Thus, after 14 days, the part of ligated obstructed ureter was resected, a polyethylene tube of 25 gages (manufactured by Nippon Sherwood) was used as a cuff and inserted into and retained at the lumen from the cut end of the lower normal ureter, then the cuff was also retained in the expanded upper ureter and each of them was ligated and fixed by 7-0 Nylon to reconstruct the urinary passage. At the same time, the right kidney at the opposite side was excised. After the release of the obstruction, body weight was measured, blood was collected on the 2nd day, 5th day and 7th day from the release to measure serum creatinine, then the rat was sacrificed under anesthetization and the left obstruction-released kidney was excised. With regard to the excised kidney, there were carried out measurement of weight of the kidney and pathological test for the kidney. When the compound of the present invention was not administered to the model, destruction of renal structure was observed in pathological and morphological investigations during the obstructed period and after release of the obstruction with a lapse of time causing thickening of glomerular Bowman's capsule wall, hyperplasia of mesangial cells, glomerular sclerosis, involution or dilation of urinary tubule, cellular infiltration to interstitial tissues and fibrosis. Cellular infiltration did not increase the CD5-positive T cells and CD11b/CD18 (ED8)-positive macrophage became dominant on the tenth day.

An in vivo biological test was carried out for the γ-lactone derivatives according to the present invention using the above models. With regard to the test compound, bulk powder of the test compound was dissolved in an aseptic physiological saline together with gum arabic and the final concentration of gum arabic was 5% (vol/vol). The concentration of the test compound 30 mg/ml was suspended in 5% gum arabic-saline solution. The preparation was subcutaneously injected at the dose of 30 mg/kg every day throughout the experiment. With regard to the test compound, there were used (9-1), (4-2) and (7-3) as the compounds of group I suppressing the SPFC production by allo-MLC stimulation, i.e., the compounds which selectively suppress the induction of effector macrophage in the presence of allo-MLC while there was used (3-2) as the compound of group II suppressing the SPFC production by LPS stimulation, i.e., the compounds which selectively suppress the induction of effector macrophage in the presence of LPS. Further, with regard to the compound of group III which suppresses the SPFC production by both allo-MLC stimulation and LPS stimulation, i.e., the compound which non-selectively suppresses the induction of effector macrophage, there was used a racemate of ethyl 2-(4-flyuorophenoxy)-5-oxo-2-tetrahydrofurancarboxylate which is the known compound.

The result is given in the following Table. In the Table, "functional classification" of the compound means the above group I, group II and group III. "Compound" means the compound bearing each of the above-mentioned compound numbers. The fact whether glomerular lesion was suppressed was judged by the ameriolation of the lesions such as thickness of wall of Bowman's capsule, hyperplasia of mesangial cells and glomerular sclerosis. The fact whether lesion of tubulointerstitial tissue was suppressed was judged by the ameriolation of the lesions such as thickness of basement membrane of tubules, cellular infiltration and fibrosis of interstitial tissue. In the table, "control" is the result when the same test as above was carried out using 5% gum arabic only which is a solvent.

TABLE 2

| Functional Classification | Compound | Case Numbers | Serum Creatinine level (mg/dl) on the 7th Day from Release of Obstruction | Rate of Cases where Glomerular Lesion was Suppressed | Rate of Cases where tubulo-interstitial Lesion was Suppressed | Weight of kidney (g) on the 7th Day from Release of Obstruction |
|---|---|---|---|---|---|---|
| Group I | (9-1) | n = 3 | 2.0 ± 0.2 | 0% (0/4) | 100% (4/4) | 3.01 ± 0.56 |
| | Control | n = 3 | 2.0 ± 0.2 | 0% (0/3) | 33% (1/3) | 2.62 ± 0.70 |
| | (4-2) | n = 4 | 2.7 ± 0.3 | 50% (2/4) | 100% (4/4) | 3.94 ± 0.32 |
| | Control | n = 4 | 2.7 ± 0.9 | 0% (0/4) | 0% (0/4) | 4.68 ± 0.66 |
| | (7-3) | n = 4 | 2.0 ± 0.6 | 25% (1/4) | 100% (4/4) | 2.72 ± 0.47 |
| | Control | n = 4 | 2.7 ± 0.9 | 25% (1/4) | 25% (1/4) | 2.69 ± 0.40 |
| Group II | (3-2) | n = 5 | 2.0 ± 0.4 | 100% (5/5) | 0% (5/5) | 4.36 ± 0.95 |
| | Control | n = 3 | 2.6 ± 0.9 | 33% (1/3) | 0% (0/3) | 5.61 ± 1.08 |
| Group III | Known Compd | n = 4 | 2.2 ± 0.2 | 75% (3/4) | 75% (3/4) | 2.73 ± 0.41 |
| | Control | n = 4 | 3.1 ± 0.8 | 0% (0/4) | 0% (0/4) | 2.21 ± 0.50 |

Both (9-1), (4-2) and (7-3) as the compounds of the group I which suppress the SPFC production by allo-MLC stimulation, i.e., the compounds which selectively suppress the induction of effector macrophage in the presence of allo-MLC and (3-2) as the compound of the group I which suppresses the SPFC production by LPS stimulation, i.e., the compound which selectively suppresses the induction of effector macrophage in the presence of SPFC showed a selective suppressive effect. Thus, the group I dominantly suppressed the lesion of tubulointerstitial tissue. The (3-2) of the group II did not suppress the lesion of tubulointerstitial tissue but suppressed the glomerular lesion only. The conventional compound belongs to the group III and, although it showed suppression, no selective suppression was observed.

In order to further confirm whether the preventive and therapeutic effect of the γ-lactone derivatives of the present invention to the target cell damage is selective, (7-3) of the group I and (6-1) of the group II were used as test compounds and they were subcutaneously injected at the dose of 30 mg/kg every day and compared with the control group. With regard to the control group, only 5% gum arabic which is a solvent was used and the same test as above was carried out.

The result is shown in the following Table wherefrom it is apparent that, in all cases combined with group I and group II compounds, lesion of glomerulus and of tubulointerstitial tissue were suppressed.

TABLE 3

| Combination of compounds | Case Numbers | Creatinine level (mg/dl) on 7th Day from Release of Obstruction | Rate of Cases where Glomerular Lesion was Suppressed | Rate of Cases where Lesion of Tubulo-interstitial Tissue was Suppressed | Weight of Kidney (g) on 7th Day from Release of Obstruction |
|---|---|---|---|---|---|
| Combined use of (7-3) and (6-1) | n = 3 | 2.1 ± 0.3 | 100% (3/3) | 100% (3/3) | 2.27 ± 0.16 |
| Control | n = 5 | 2.5 ± 0.7 | 0% (0/5) | 20% (1/5) | 2.55 ± 0.45 |

TEST EXAMPLE 4

Evaluation Using Puromycin Chronic Nephrosis Model in Rat

Male SD rat of 8 weeks age of about 250 g was used and 50 µg/kg of puromycin were intravenously administered once according to a method of Diamond, et al. (J. R. Diamond, I. Pesek, S. Ruggeri, M. J. Karnovsky: Essential fatty acid deficiency during acute puromycin nephrosis ameliorates late renal injury. Am. J. Physiol, 257:F798~F807, 1989). There was induced a chronic puromycin nephrosis rat where albuminuria increased from about tenth to twelfth week. After eighth week from administration of puromycin, each of compound (9-1) and compound (6-1) was subcutaneously injected at the dose of 30 mg/kg/day everyday until the 22nd week. Incidentally, as shown in the above Table 1, (9-1) is a compound which suppresses the SPFC production by allo-MLC stimulation or, in other words, a compound which selectively suppresses the induction of effector macrophage in the presence of allo-MLC (group I) while (6-1) is a compound which suppresses the SPFC production by LPS stimulation or, in other words, a compound which selectively suppresses the induction of effector macrophage in the presence of LPS (group II).

As a functional evaluation of kidney, albumin in urine was measured every week using a kit for the measurement of albumin. On the 22nd week, the rat was killed and anatomized to observe functional and morphological changes of kidney.

The result is shown in the following Table. The compound (1-1) (group I) well suppressed the lesion of tubulointerstitial tissues while the compound (2-1) (group II) well suppressed the glomerular lesion. Functional average daily albuminuria was proportional to the morphological change.

Accordingly, it was found that the compounds of the group I which suppressed the induction of effector macrophage by allo-MLC stimulation selectively suppressed the lesion of tubulointerstitial tissues while the compounds of the group II which suppressed the induction of effector macrophage by LPS stimulation selectively suppressed the glomerular lesion.

TABLE 4

| Functional Classification | Compound | Case Numbers | Albumin in Urine (mg/day) | Rate of Cases where Glomerular Lesion was Suppressed | Rate of Cases where Lesion of Tubulointerstitial Tissue was Suppressed |
|---|---|---|---|---|---|
| Group I | (9-1) | n = 6 | 20, 7, 5, 5, 5, 4 | 50% (3/6) | 83% (5/6) |
| Group II | (6-1) | n = 6 | 56, 20, 11, 7, 4, 3 | 67% (4/6) | 17% (1/6) |

Correlation between the structural characteristic of immunosuppressive γ-lactone derivative and biological activities in vitro and in vivo is given.

TABLE 5

| | | Activity in vitro | | Activity in vitro | | |
|---|---|---|---|---|---|---|
| Structure-Characteristic of compound | Compound | Inhibiting Concentration for SPEC Production by allo-MLC Stimulation ($\mu$M: $IC_{50}$) | Inhibiting Concentration for SPEC Production by LPS Stimulation ($\mu$M: $IC_{50}$) | Suppressive Effect to Glomerular Lesion | Suppressive Effect to Lesion of Tubulointerstitial Tissue | Experimental Model of Rat |
| A | (3-2) | >1.0 | 1 | o | x | UUO/Release |
|   | (4-2) | 0.01 | >1.0 | Δ | o | UUO/Release |
| C | (6-1) | >1.0 | 0.001 | o | x | CPN |
|   | (6-2) | not done | 0.001 | o | x | UUO/Release |
| D | (7-3) | 0.01 | 0.01 | x | o | UUO/Release |
| Metabolite (9) |   | 0.01 | >1.0 | x | o | UUO/Release |
| Conventional Compound |   | 0.1 | 0.1 | o | o | UUO/Release and CPN | o: available
Δ: somewhat available
x: not available
UUO/Release: ureter was obstructed for 14 days followed by releasing
CPN: chronic PAN nephrosis As such, the γ-lactone derivatives in accordance with the present invention are able to selectively suppress the induction of effector macrophage by allo-MLC stimulation and the induction of effector macrophage by LPS stimulation. It has been also proved that, as a result thereof, a suppressive effect depending upon the lesion is able to be achieved.

Accordingly, pharmaceutical preparations containing the γ-lactone derivatives according to the present invention can be applied depending upon the lesions. When, for example, the progressive lesion after the renal damage comes to glomerulus in the case of renal diseases, administration of the pharmaceutical containing the compound of the group II is effective. On the other hand, when the progressive lesion after the renal damage comes to tubulointerstitial tissue, administration of the pharmaceutical containing the compound of the group I is effective. When the progressive lesion after the renal damage comes to both glomerulus and tubulointerstitial tissue, combination use of the pharmaceutical containing the compounds of the above-mentioned groups I and II is effective. When the progressive lesion after pancreatic damage comes to islets of Langerhans in the case of the pancreatic disease, administration of the pharmaceutical containing the compound of the group II is effective while, when the progressive lesion after pancreatic damage comes to exocrine, acinar and ductal interstitial tissue of pancreas, administration of the pharmaceutical containing the compound of the group I is effective. When the progressive lesion after the renal damage comes to both islets of Langerhans and exocrine, acinar and ductal interstitial tissue of pancreas, combination use of the pharmaceutical containing the compounds of the above-mentioned groups I and II is effective.

As mentioned above, the γ-lactone derivatives in accordance with the present invention achieve a selective suppressive action unlike the conventional compounds. As a result of such an action, the γ-lactone derivatives in accordance with the present invention only suppress the activation of induction of effector macrophage acting in a cytotoxic manner to damaged organ tissue cells and do not suppress the activation of induction of macrophage participating in the regeneration of tissues and, therefore, they are able to more effectively prevent or cure the progressive lesion after the organic damage without lowering the defensive ability of organism.

It has been also found that the compound (9-1), i.e. ethyl 2-ketoglutarate, is one of the active metabolite derived from the compounds of the group I which selectively suppress the SPFC production by allo-MLC stimulation. Such an active metabolite shows an activity for suppressing the lesion of in tubulointerstitial tissue in vivo. Similarly, the compound (9-2), i.e. benzyl 2-ketoglutarate, is one of the active metabolite of the group II which selectively suppresses the SPFC production by LPS stimulation and is able to suppress the lesion of glomerulus in vivo.

TEST EXAMPLE 5

Acute and Chronic Toxicity Tests

Toxicity test of benzyl 2-chloro-5-oxotetrahydrofuran-2-carboxylate represented by the formula (6-1) manufactured in Example 8 and ethyl 2-ketoglutarate represented by the formula (9-1) was carried out. To be more specific, the former and the latter were subcutaneously injected at the doses of 30 mg/kg/day and 90 mg/kg/day, respectively for ten days and their toxicity was investigated whereupon there was only noted an increase in weights of the liver and the spleen in a light degree.

When both were administered at the dose of 30 mg/kg/day for consecutive 14 days, neither reduction of body weight nor death was noted and there was no abnormality at the subcutaneously injected area whereupon they were found to be of low toxicity.

PREPARATION EXAMPLE 1

| (Tablets) | |
|---|---|
| (1) Benzyl 2-chloro-5-oxotetrahydrofuran-2-carboxylate | 10 g |
| (2) Lactose | 90 g |
| (3) Corn starch | 29 g |
| (4) Magnesium stearate | 1 g |
| | 130 g |

The components (1) and (2) and 24 g of the component (3) were mixed with water to granulate, the resulting granules were mixed with 5 g of the component (3) and the component (4), and the mixture was compressed using a compressive tabletting machine to manufacture 1,000 tablets of 7 mm diameter containing 10 mg of the component (1) per tablet.

PREPARATION EXAMPLE 2

| (Capsules) | |
|---|---|
| (1) Benzyl 2-chloro-5-oxotetrahydrofuran-2-carboxylate | 50 mg |
| (2) Lactose | 14 mg |
| (3) Corn starch | 29 mg |
| (4) Hydroxypropyl cellulose | 6 mg |
| (5) Magnesium stearate | 1 mg |
| | 100 mg per capsule |

The above-mentioned components (1), (2), (3) and (4) were mixed and granulated according to a conventional method. The component (5) was added thereto and placed into a gelatin capsule by a conventional method to give a capsule preparation.

INDUSTRIAL APPLICABILITY

The present invention is able to provide a method for the induction of effector macrophage which is induced and activated corresponding to the lesion inherent to the tissues after organic lesion and results in a progressive lesion after the organic damage.

By utilizing the said method, the present invention is able to provide a method for screening compounds which are able to prevent, mitigate or cure the progressive lesion after organic damage such as glomerular lesion and tubulointerstitial lesion in the case of kidney and, in the case of pancreas, exocrine interstitial lesion or pancreatitis and Langerhans islet lesion or diabetes. The present invention also provides a method for screening compounds which are able to prevent, mitigate or cure diabetes and diabetic retinitis or pancreatitis and tubulointerstitial lesion complicated with pancreatitis at the same time.

It is also possible to provide a pharmaceutical for the prevention or the therapy of the above-mentioned progressive lesion after the organic damage or a therapeutic method therefor by utilizing the said screening method. The said pharmaceutical or the said therapeutic method has little side effect such as an unnecessary lowering of defense of organism or induction of new tissue damage and, in addition, it achieves repair and regeneration of the tissues without unnecessary lowering of the defense of organism whereby it is now possible to conduct the therapy for a long period on a continuous basis using the said pharmaceutical or therapeutic method.

The novel γ-lactone derivatives according to the present invention are compounds which are able to selectively suppress the induction of effector macrophage corresponding to the lesion inherent to the tissues after the organic damage and are able to be used as the above-mentioned pharmaceutical.

The novel γ-lactone derivatives according to the present invention have a selective induction-suppressive action for the above effector macrophage and, as a result, they show a selective immunosuppressive action or a fibrosis inhibiting action to specific tissues. Accordingly, the novel γ-lactone derivatives according to the present invention are able to be used not only as the above-mentioned pharmaceutical but also as an immunosuppressant or a fibrosis inhibitor. To be more specific, the pharmaceutical containing the novel γ-lactone derivative of the present invention is able to selectively suppress the progress or worsening of the diseases to the target organ or the like and, since its immunosuppressive action or fibrosis inhibiting action is strong, it is effective for therapy and/or prevention of rejection reaction upon of xenogenic or allogeneic cell, tissue or organ transplantation and endotoxin shock reaction by bacterial toxin, systemic intravascular coagulation, various inflammatory diseases, chronic inflammatory diseases and cancer. To be more specific, the pharmaceutical containing the novel γ-lactone derivative according to the present invention is able to be used for prevention of onset or progress of rejection reaction upon transplantation of allogeneic or xenogenic organs, cells or tissues, or acute or chronic glomerular nephritis and onset or progress of interstitial retinitis or diabetes; therapy and/or prevention of complications such as diabetic nephropathy, diabetic retinopathy and diabetic neuropathy; therapy and/or prevention of chronic pancreatitis, arteriosclerosis, arteriosclerotic restenosis, pulmonary fibrosis, dialytic amyloidosis, chronic hepatitis, cerebrospinal degeneration, asthma, rheumatic arthritis, chronic pigmentary skin diseases, psoriasis, autoimmune chronic organic tissue damage, endotoxin shock reaction by cytotoxin, systemic intravascular coagulation or cancer or its metastasis; and prevention and therapy of infection of AIDS virus. It is also able to be used as a substitute for steroidal therapeutic agent.

What is claimed is:

1. A pharmaceutical composition, which comprises an active ingredient that selectively suppresses the induction of effector macrophages selected from the group consisting of:

(i) an optical isomer γ-lactone represented by the formula (3):

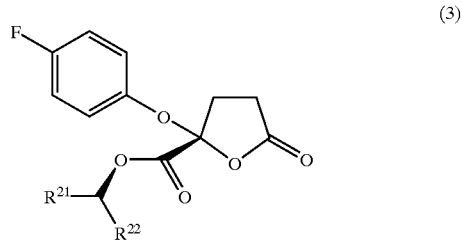

or an optical isomer γ-lactone represented by the formula (4):

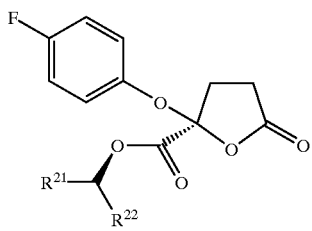

(4)

wherein, $R^{21}$ is an optionally substituted naphthyl group, $R^{22}$ is an optionally substituted straight or branched hydrocarbon residue having 1 to 6 carbon atoms, or a mixture of said optical isomers represented by the formulae (3) and (4);

(ii) one of said optical isomers represented by the formula (3) or (4), or a mixture of said optical isomers represented by the formulae (3) and (4), wherein $R^{21}$ is naphthyl and $R^{22}$ is methyl;

(iii) a compound represented by the formula (5):

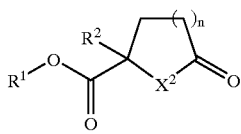

(5)

wherein, (a) $R^1$ and $R^2$ may be the same or different and each is hydrogen, an open-chain aliphatic hydrocarbon group which may be substituted or interrupted by an intervening group, an optionally substituted cyclic aliphatic hydrocarbon group, an optionally substituted aryl group, an optionally substituted heterocyclic group or an optionally substituted condensed heterocyclic group;

$X^2$ is O, S or $NR^3$ in which $R^3$ is hydrogen, oxygen, an open-chain aliphatic hydrocarbon group which may be substituted or interrupted by an intervening group, an optionally substituted cyclic aliphatic hydrocarbon group, an optionally substituted aryl group, an optionally substituted heterocyclic group or an optionally substituted condensed heterocyclic group; and n is an integer from 1 to 5; or (b) $X^2$ is O, S or $NR^3$, $R^1$, $R^2$ and $R^3$ each is a substituent represented by the formula $R^{10}$—Z—$R^{11}$—, wherein $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group, and Z is an intervening group; and n is an integer from 1 to 5, or a pharmacologically acceptable salt thereof;

(iv) a compound represented by the formula (6):

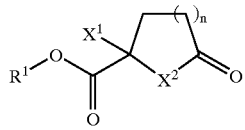

(6)

wherein, $R^1$, $X^2$ and n have the same meanings as defined above, $X^1$ is halogen, cyano group, an optionally substituted mercapto group, an optionally substituted sulfo group, an optionally substituted sulfonyl group, an optionally substituted hydroxyl group, an optionally substituted amino group or an optionally substituted phosphoryl group, or a pharmacologically acceptable salt thereof; and (v) a compound represented by the formula (7):

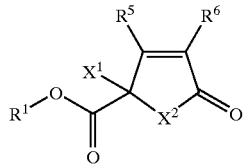

(7)

wherein, $R^1$, $X^1$ and $X^2$ have the same meanings as defined above, $R^5$ and $R^6$ may be the same or different and each is (a) hydrogen, a straight or branched aliphatic hydrocarbon group which may be substituted or interrupted by an intervening group, an optionally substituted cyclic aliphatic hydrocarbon group, an optionally substituted heterocyclic group, or an optionally substituted condensed heterocyclic group;

(b) a substituent represented by the formula $R^{10}$—Z—$R^{11}$, wherein $R^{10}$ and $R^{11}$ may be the same or different and each is an optionally substituted open-chain or cyclic hydrocarbon group, an optionally substituted aryl group, an optionally substituted heterocyclic group or an optionally substituted condensed heterocyclic group; and Z is an intervening group; or (c) $R^5$ and $R^6$ together with the carbon atom to which they are attached form an optionally substituted aromatic ring;

or a pharmacologically acceptable salt thereof.

2. The pharmaceutical composition according to claim 1, wherein the active ingredient is selected from the group consisting of:

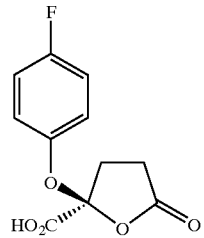

(1)

-continued

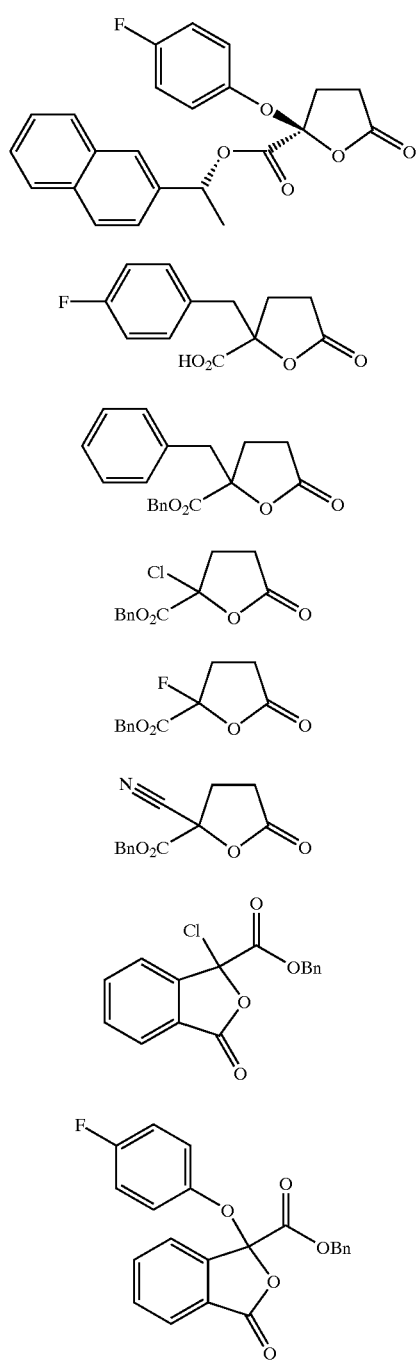

and

-continued

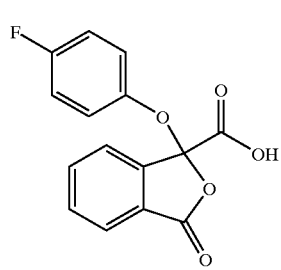

wherein Bn is benzyl.

3. The pharmaceutical composition according to claim 1 or 2, wherein the active ingredient is represented by the formula (4-2):

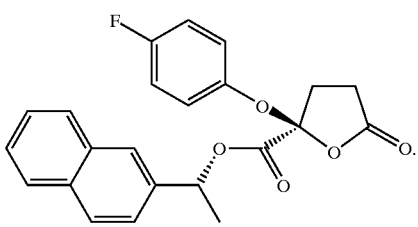

4. The pharmaceutical composition according to claim 1 or 2, wherein the active ingredient is represented by the formula (6-2):

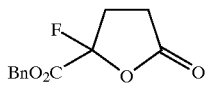

wherein Bn is benzyl.

5. The pharmaceutical composition according to claim 1 or 2, wherein the active ingredient is represented by the formula (7-3):

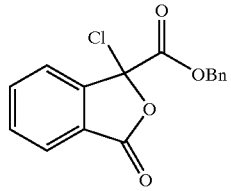

wherein Bn is benzyl.

6. The pharmaceutical composition according to claim 1, wherein the active ingredient is represented by the formula (7), wherein $R^5$ and $R^6$ together with the carbon atom to which they are attached form an optionally substituted aromatic ring, $X^2$ is O, $X^1$ is optionally substituted hydroxyl and $R^1$ is hydrogen.

* * * * *